(12) United States Patent
Giraud et al.

(10) Patent No.: US 9,079,729 B2
(45) Date of Patent: Jul. 14, 2015

(54) STRIP DISPENSER AND STRIPS FOR USE WITH THE SAME

(75) Inventors: Jean-Pierre Giraud, Auburn, AL (US); Herve Pichot, Chennevieres-sur-Marne (FR); Joel Francisco, Noisey le Grand (FR)

(73) Assignee: CSP Technologies, Inc., Auburn, AL (US)

( * ) Notice: Subject to any disclaimer, the term of this patent is extended or adjusted under 35 U.S.C. 154(b) by 95 days.

(21) Appl. No.: 14/006,349

(22) PCT Filed: Mar. 12, 2012

(86) PCT No.: PCT/US2012/028773
§ 371 (c)(1),
(2), (4) Date: Dec. 9, 2013

(87) PCT Pub. No.: WO2012/138451
PCT Pub. Date: Oct. 11, 2012

(65) Prior Publication Data
US 2014/0086796 A1 Mar. 27, 2014

Related U.S. Application Data

(60) Provisional application No. 61/473,524, filed on Apr. 8, 2011.

(51) Int. Cl.
*B65H 1/04* (2006.01)
*B65H 1/08* (2006.01)
(Continued)

(52) U.S. Cl.
CPC ...... *B65H 1/04* (2013.01); *B65D 83/08* (2013.01); *B65D 83/0829* (2013.01);
(Continued)

(58) Field of Classification Search
CPC .............. G01N 33/48757; G01N 2035/00089; G01N 2035/00039; G01N 33/48778; B65D 83/0829; B65D 83/087; B65D 47/0804; B65D 83/0418; B65H 3/24; B65H 1/00; B65H 2402/41; B01L 2300/0825; B01L 9/52
USPC ......... 422/68.1, 430, 547, 554, 401; 221/197, 221/198, 242, 287
See application file for complete search history.

(56) References Cited

U.S. PATENT DOCUMENTS

| 4,190,420 A | 2/1980 | Covington et al. |
|---|---|---|
| 4,850,511 A | 7/1989 | Kral et al. |

(Continued)

OTHER PUBLICATIONS

International Search Report and Written Opinion for International Patent Application No. PCT/US2012/028773, mailed Jun. 12, 2012.

*Primary Examiner* — Melanie Y Brown
*Assistant Examiner* — Erik B Crawford
(74) *Attorney, Agent, or Firm* — David B. Gornish

(57) ABSTRACT

The present invention relates to product dispensers, and in particular dispensers for products in the form of strips. The product dispenser includes a container having a lid that may be pivotally attached to a base. According to an embodiment, the assembly includes a cartridge housing and a dispensing cartridge. The dispensing cartridge is configured to house a stack of strips. A guide is biased by a spring to push a presser bar against the bottom portion of the stack of the strips toward the dispensing end of the assembly. When a strip is to be dispensed, a slider is moved from a first position to a second position, causing a slider arm to contact and assist in rotating a strip toward a dispensing opening. At least a corner of the rotated strip may protrude through the dispensing opening so that a user may remove the strip from the assembly.

21 Claims, 27 Drawing Sheets

(51) Int. Cl.
  *B65H 1/12* (2006.01)
  *B65H 1/14* (2006.01)
  *B65D 83/08* (2006.01)
  *B65D 85/62* (2006.01)
  *G01N 35/00* (2006.01)
  *G01N 33/487* (2006.01)

(52) U.S. Cl.
  CPC ............ *B65D 85/62* (2013.01); *B65H 1/08*
    (2013.01); *B65H 1/12* (2013.01); *B65H 1/14*
    (2013.01); *G01N 33/48757* (2013.01); *G01N*
    *35/00029* (2013.01); *B65D 2251/20* (2013.01);
              *G01N 2035/00108* (2013.01)

(56) References Cited

U.S. PATENT DOCUMENTS

| | | | |
|---|---|---|---|
| 2002/0076349 A1* | 6/2002 | Aitken et al. | 422/58 |
| 2002/0104849 A1* | 8/2002 | Giruad | 221/270 |
| 2003/0089730 A1* | 5/2003 | May et al. | 221/232 |
| 2004/0178216 A1* | 9/2004 | Brickwood et al. | 221/268 |
| 2007/0034640 A1 | 2/2007 | Casale | |
| 2008/0021296 A1 | 1/2008 | Creaven | |
| 2008/0135568 A1 | 6/2008 | Giraud et al. | |
| 2008/0217354 A1* | 9/2008 | Newman et al. | 221/229 |
| 2009/0098018 A1* | 4/2009 | Bainczyk et al. | 422/68.1 |

\* cited by examiner

STRIP DISPENSER AND STRIPS FOR USE WITH THE SAME

FIELD OF INVENTION

The present invention relates to product dispensers, and in particular dispensers for products in the form of strips.

BACKGROUND

Product dispensers used for consumer products in the form of strips are often disposable such that after the product contained therein has been used or is to be discarded, the entire product dispenser is discarded. Additionally, while such dispensers may include a seal that is used to enhance the shelf life of the product, the seal may be removed after the initial opening of the dispenser, or a more permanent seal may become compromised or degrade in quality through the repeated opening and closing of the product dispenser.

Embodiments of the present invention relate to product dispensers for consumer products in the form of strips, including, for example, pharmaceutical products and supplies, confectionaries, and smokeless tobacco, among other products. Moreover, the present invention relates to reusable product dispensers that are configured to allow for the refilling of consumer products, such as, for example, glucose strips. According to certain embodiments, the product dispenser may be refilled with the selected consumer products by replacing the consumer productions with, or without, replacing other components of the product dispenser. Additionally, according to certain embodiments, the product dispenser may include replaceable seals that assist in controlling the ingress and/or egress of moisture into/out of an interior space of the product dispenser, and which may be used to control the conditions in an interior space of the product dispenser.

SUMMARY

An aspect of the invention is a dispenser assembly that includes a container having a base and lid. The base has a bottom wall and a side wall that generally define an interior space. According to certain embodiments, the base and lid may be joined together by a hinge. The assembly also includes a cartridge housing that is positioned within the interior space of the base. The assembly also includes a dispensing cartridge having a dispensing end, a feeding end, and an interior. At least a portion of the dispensing cartridge is positioned within a recess of the cartridge housing. The interior of the dispensing cartridge is configured to receive the placement of a stack of strips. Further, the dispenser cartridge has a dispensing opening that is configured to dispense a strip from the stack of strips. A pusher bar is at least partially positioned in the interior of the dispensing cartridge. The assembly also includes a guide that is biased by a first spring to press the pusher bar toward the dispensing end of the dispensing cartridge. Additionally, the assembly includes a slider having a dispensing arm. At least a portion of the slider is housed in a channel formed in the cartridge housing. The channel is configured for the slideable movement of the slider from a first, non-dispensing, position to a second, dispensing, position.

Another aspect of the invention is dispenser assembly that includes a container having a base and a lid. According to certain embodiments, the base and lid may be joined by a hinge. The base has a bottom wall and a side wall that generally define an interior space. The assembly also includes an attachment member that is operably secured to the base. The attachment member has a first end, a second end, a guide slot, and an interior region. Additionally, the assembly includes a cartridge having a bottom portion and at least one grip. The cartridge is configured to receive the placement of a stack of strips on the bottom portion of the cartridge. The at least one grip is configured to secure the cartridge to the attachment member. The assembly further includes a guide that is operably attached to a first end of a first spring. At least a portion of the guide is configured to move along at least a portion of the guide slot. The first spring is configured to bias the guide toward the first end of the attachment member. A pusher bar is positioned adjacent to the guide and is pressed by the guide toward the first end of the attachment member. The assembly also includes a cover that is configured to cover at least a portion of the cartridge. The cover includes a dispensing opening, at least one orifice, and a slot. The at least one orifice is configured to receive the protrusion of at least a portion of the at least one grip. Further, the assembly includes a slider having a slider arm, the slider being configured to slide from a first position to a second position along the slot of the cover. The slider arm is configured to engage a strip from the stack of strips as the slider moves from the first and second position.

Another aspect of the invention is a dispenser assembly that includes a container having a lid and a base, the base having an interior region. According to certain embodiments, the base and lid may be joined by a hinge. The assembly also includes an inner receptacle that is positioned within the interior region of the base. The inner receptacle includes a lever, a sidewall, and an interior area. The lever is configured to be displaced by a user from a first position to a second position. The assembly also includes a flexible member that is secured to the outer and/or inner receptacle. Further, the assembly has a pusher blade having a first end and a second end, the first end being operably connected to the lever. Additionally, the assembly has a guide housing, at least a portion of the guide housing being positioned within the inner region of the inner receptacle. The guide housing includes a slot that is configured to guide at least a portion of the pusher blade as the lever is moved from the first portion to the second position. The assembly also includes a dispenser housing having an upper portion, a body portion, and a slot. The body portion has an interior region configured to receive the insertion of a stack of strips. The upper portion includes a dispensing opening that is configured for dispensing one or more strips from the stack of strips. The slot is configured to receive the insertion of the second end of the pusher blade when the lever is moved to the second position. Further, at least a portion of the dispenser housing is positioned within the inner region of the inner receptacle. The assembly further includes a guide that is biased by a spring to press a pusher bar across at least a portion of the interior region of the body portion toward the upper portion of the dispenser housing.

The assemblies of the present invention may also include a seal that may control and/or prevent the ingress of moisture into the assembly or control the conditions within the assembly. Further, the assemblies may also include interface electronics that may be used to detect information and/or process information detected on dispensed strips that have been used by a user, such as, for example, glucose strips, among others. Additionally, individual components of the assemblies may be refillable and/or disposable and so that the component may be reused or replaced.

DETAILED DESCRIPTION

Figure 1:
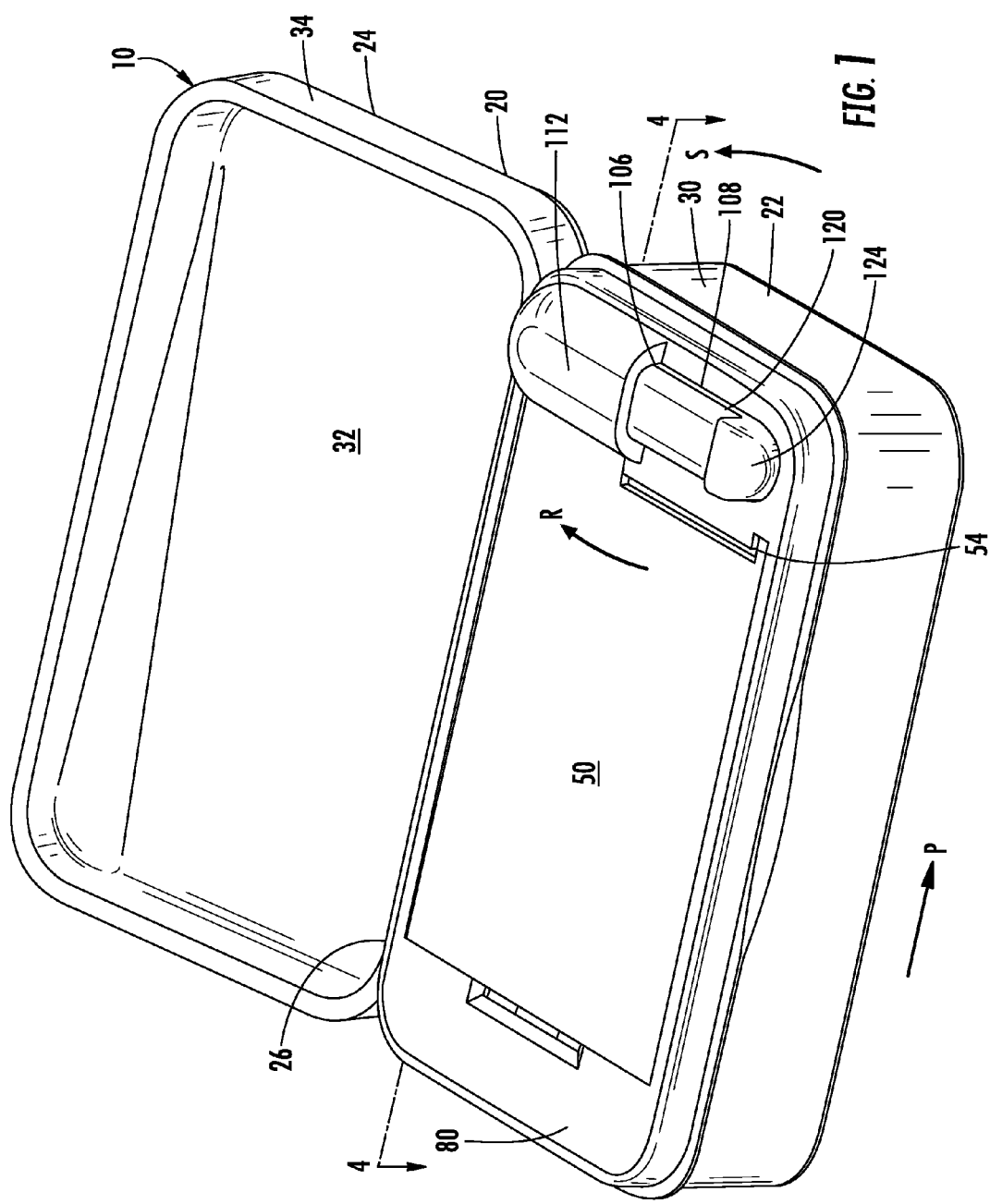
FIG. 1 is a top perspective view of an embodiment of the dispenser in a starting position.

Certain terminology is used in the foregoing description for convenience and is not intended to be limiting. Words such as "front," "back," "top," and "bottom" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

A first embodiment of a dispenser assembly 10 is shown in FIGS. 1-5. As shown, the assembly 10 generally includes a container 20, a dispensing cartridge 50, and a cartridge housing 80. The assembly 10 houses a stack 11 of strips 12 and can be used to dispense individual ones of the strips 12.

Figure 2:
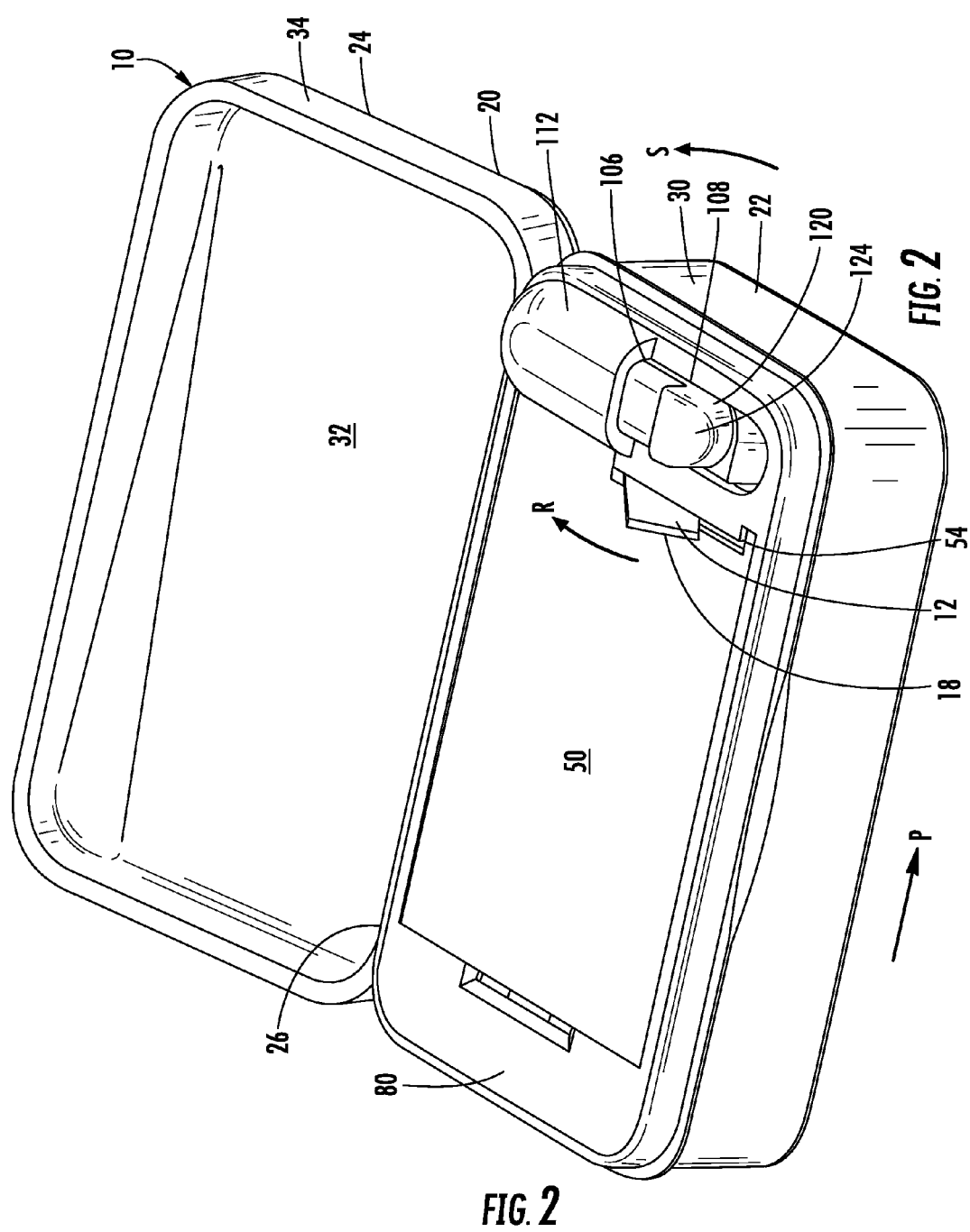
FIG. 2 is a top perspective view of the dispenser of FIG. 1 in dispensing position.
Figure 3:
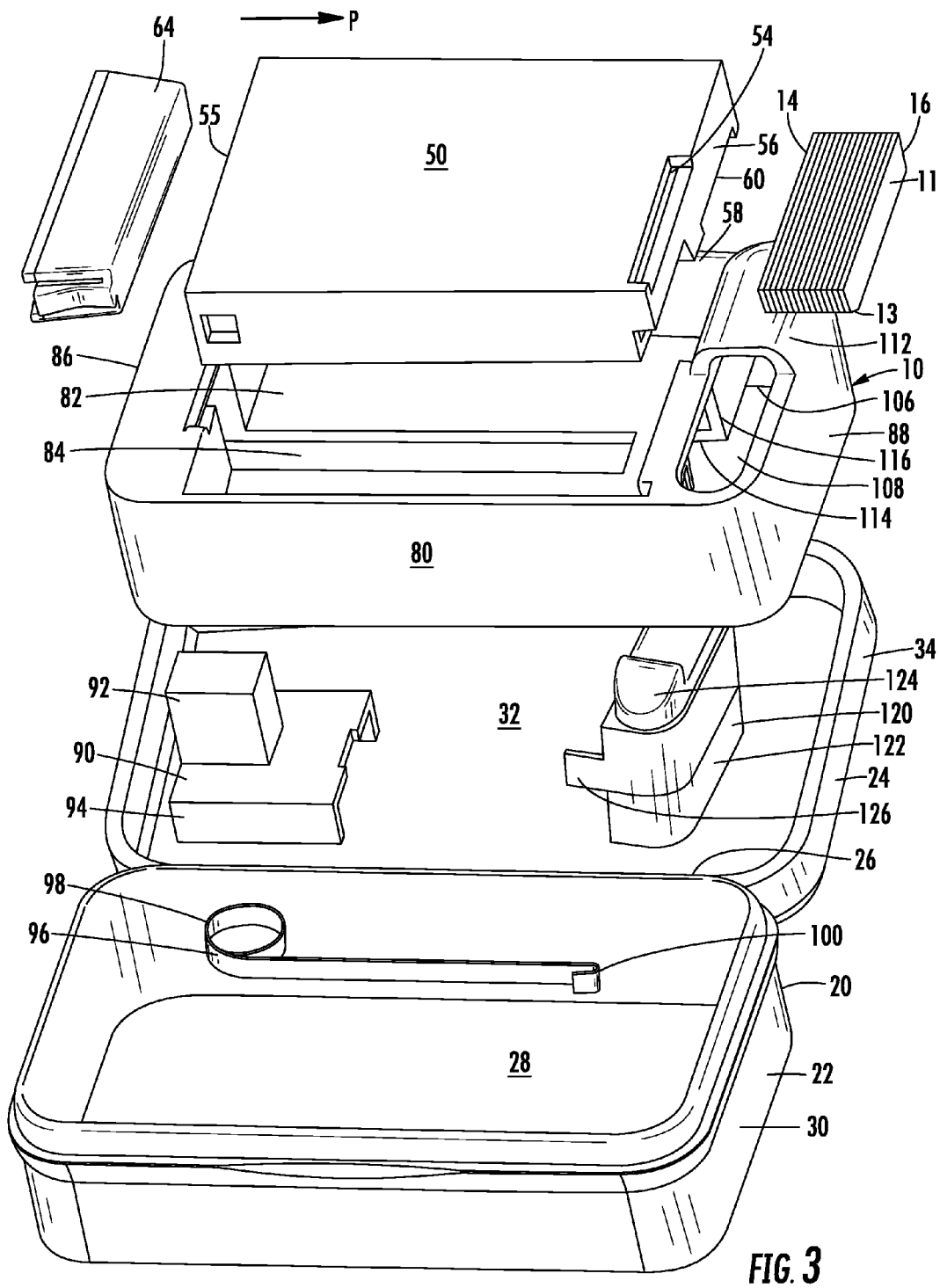
FIG. 3 is an exploded view of the dispenser, as shown in FIG. 1.
Figure 4:
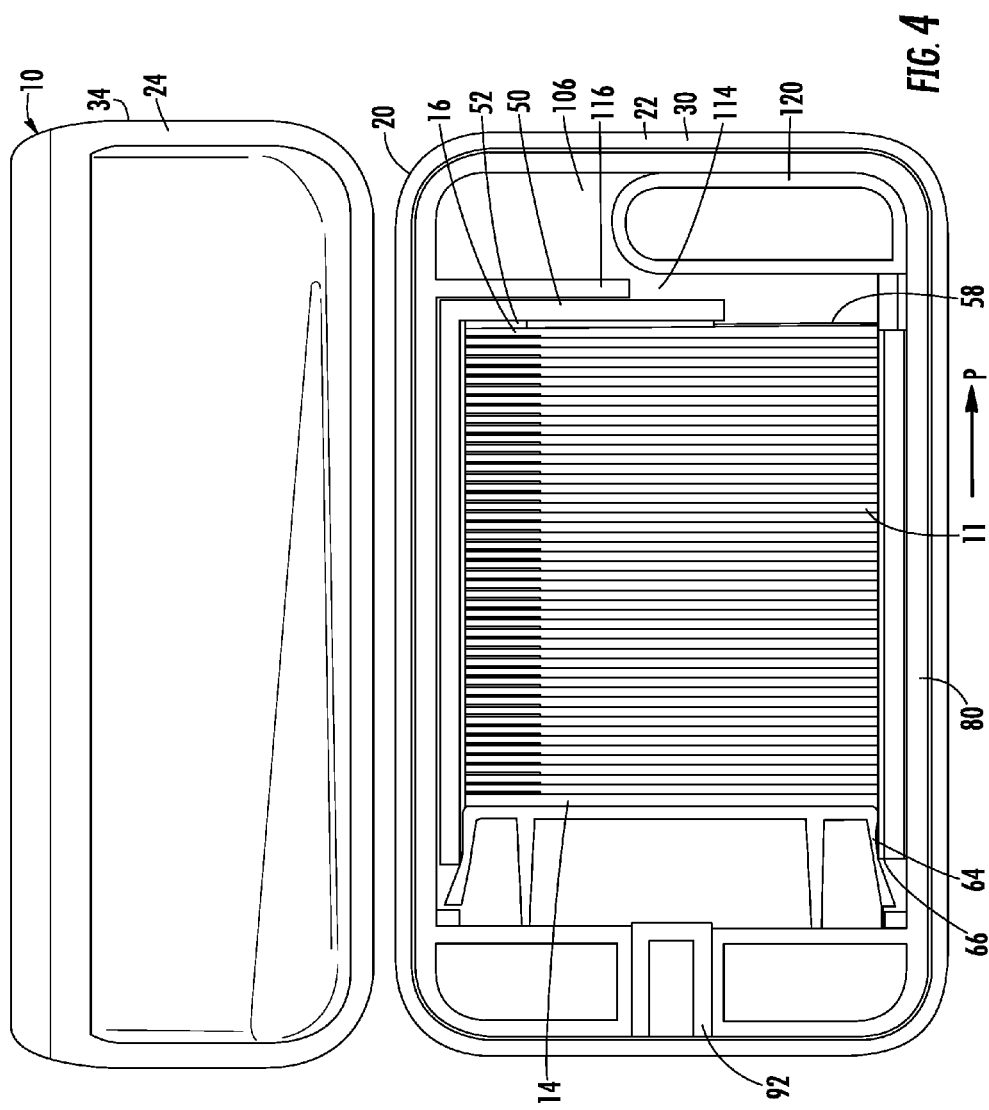
FIG. 4 is a cross section taken along line 4-4 in FIG. 1.

Referring to FIGS. 1-3, the container 20 is shown in detail. As shown, the container 20 includes a base 22 and a lid 24 pivotally attached to the base 22 at a hinge 26. The base 22 includes a bottom wall 28 and a side wall 30 extending upwardly from the bottom wall 28 about the perimeter thereof. The bottom wall 28 and side wall 30 together define an interior space for containing the dispensing cartridge 50 and cartridge housing 80. The lid includes a top wall 32 and a side wall 34 depending downwardly from the top wall 32 about the perimeter thereof. The lid 24 pivots about the hinge 26 between an opened position, shown in FIGS. 1-3, and a closed position in which the lid side wall 34 contacts the base side wall 28.

As shown in FIGS. 1-4, the container 20 holds the dispensing cartridge 50 and dispensing cartridge housing 80. The dispensing cartridge 50 and dispensing cartridge housing 80 work in conjunction to dispense individual strips 12 from a stack contained within the cartridge 50, as described in detail below.

Referring to FIGS. 3, 4, 7A and 7B, the dispensing cartridge 50 is shown in detail. As shown, the dispensing cartridge 50 has a substantially rectangular shape and defines an interior 52 for housing a stack 11 of strips 12. The cartridge 50 is preferably shaped to conform to the shape of the stack 11, which is also substantially rectangular in the illustrated embodiment. It should be understood that the shape of the cartridge 50 could be modified to accommodate other product shapes as well. A pusher bar also 64 sits within the interior 52 of the cartridge 50 at a feeding end 14 of the stack 11 of strips 12 and pushes the stack in direction P, towards a dispensing opening 54 of the cartridge 50, as explained in detail below. The term "dispensing end," as used hereinafter with respect to any element described herein, shall refer to the end of that element situated towards the right, or oriented towards direction P, in FIGS. 1-3. The term "feeding end," as used hereinafter with respect to any element of the invention, shall refer to the end of that element situated towards the left, or oriented in the opposite direction as (away from) direction P, in FIGS. 1-3. As shown in FIGS. 1 and 2, individual strips 12 at a dispensing end 16 of the stack 11 are dispensed through the dispensing opening 54, which is located on an upper surface of the cartridge 50 at a dispensing end 56 thereof.

Figure 7A:
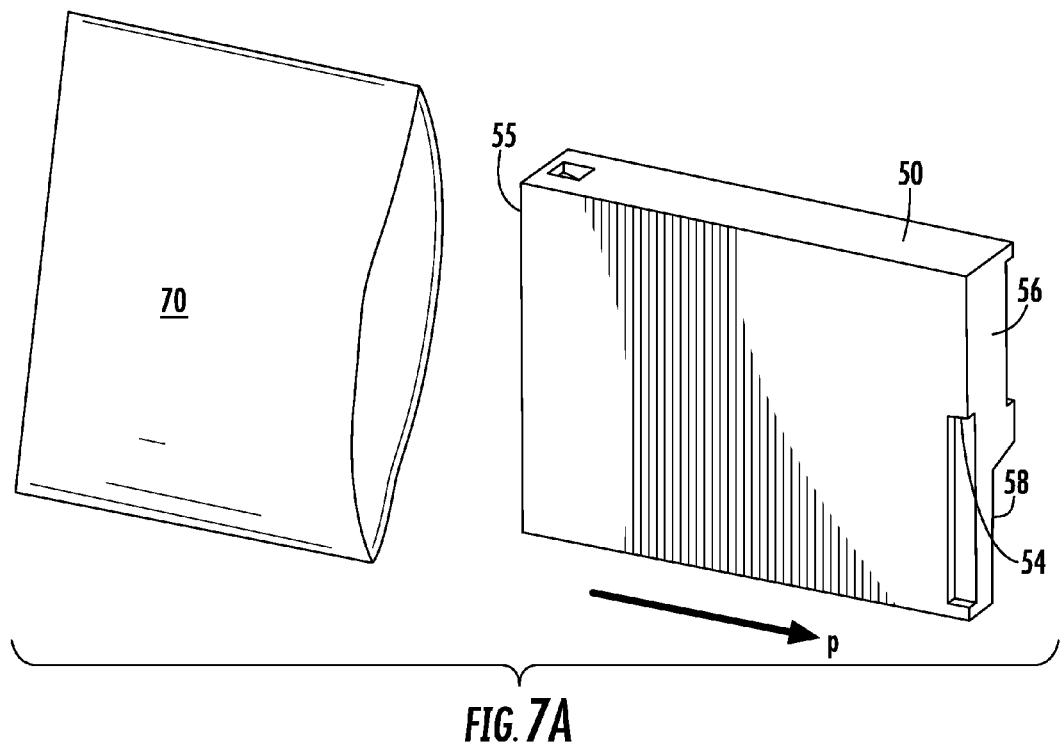
FIG. 7A is a top perspective view of a dispensing cartridge and packaging for use with the dispenser of FIG. 1.
Figure 7B:
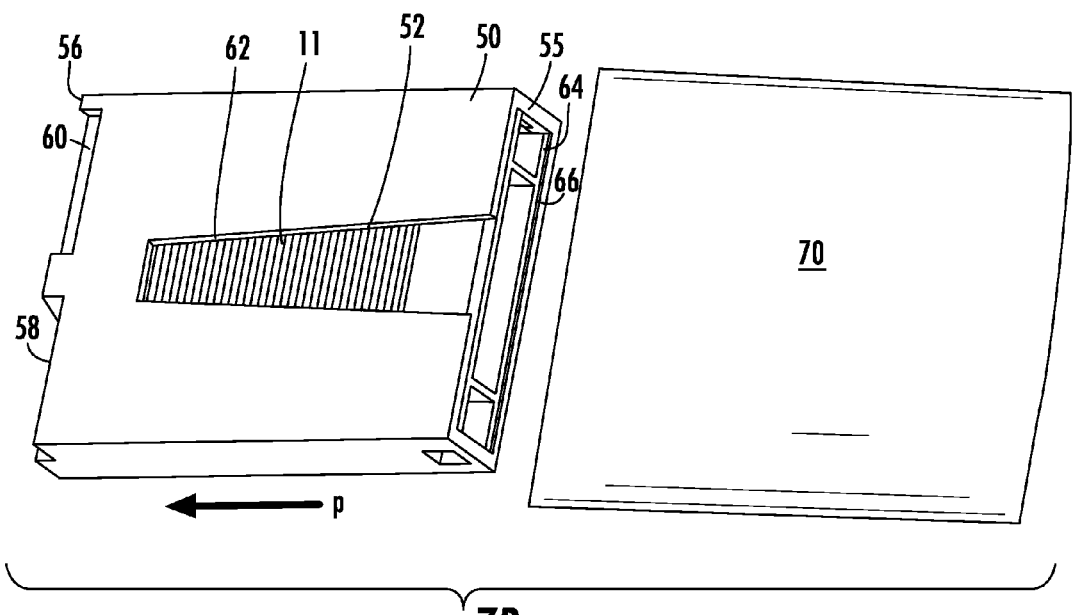
FIG. 7B is a bottom perspective view of a dispensing cartridge and packaging for use with the dispenser of FIG. 1.

As shown in FIG. 7B, the bottom of the dispensing cartridge 50 includes a guide slot 62. The guide slot 62 receives a guide rail 92 that pushes the pusher bar 64 in direction P, in turn pushing the stack 11 of strips 12 in direction "P." An access opening 66 is provided at the feeding end 55 of the cartridge 50 to permit entry of the guide rail 92. The bottom of the dispensing cartridge 50 further includes a clearance slot 60, located towards the rear of the cartridge 50 at the dispensing end 56 thereof to allow for pivoting of the strips 12 during dispensing, as well as a slider arm slot 58 that receives a slider arm 126 to actuate a dispensing operation of the dispenser assembly 10. According to an embodiment, at least a portion of the slider arm 126 that engages with a strip 12 during dispensing may have a configuration that assists with the pivoting of the strip 12, such as an angled, chamfered, or round shaped, among others.

The cartridge 50 sits within a recess 82 formed in the cartridge housing 80, which in turn sits within the base 22 of the container 20. As shown in FIG. 3, the cartridge housing 80 includes a guide slot 84 that aligns with the guide slot 62 of the cartridge 50, when the cartridge 50 is in place within the recess 82 of the cartridge housing 80. A guide 90 including guide rail 92 sits beneath the cartridge housing 80 within the container base 22. The guide rail 92 protrudes upward from a body portion 94 of the guide 90 and extends through the aligned guide slots 62, 84 of the cartridge 50 and cartridge housing 80, coming into contact with a feeding end of the pusher bar 64, to push the pusher bar 64 in direction P, which in turn pushes the stack 11 of strips 12 in direction P. Tracks 146, 148 may be provided in the bottom surface of the cartridge housing 80, to direct the guide 90 in a straight line towards the dispensing end 56 of the cartridge 50, in direction P.

Figure 5:
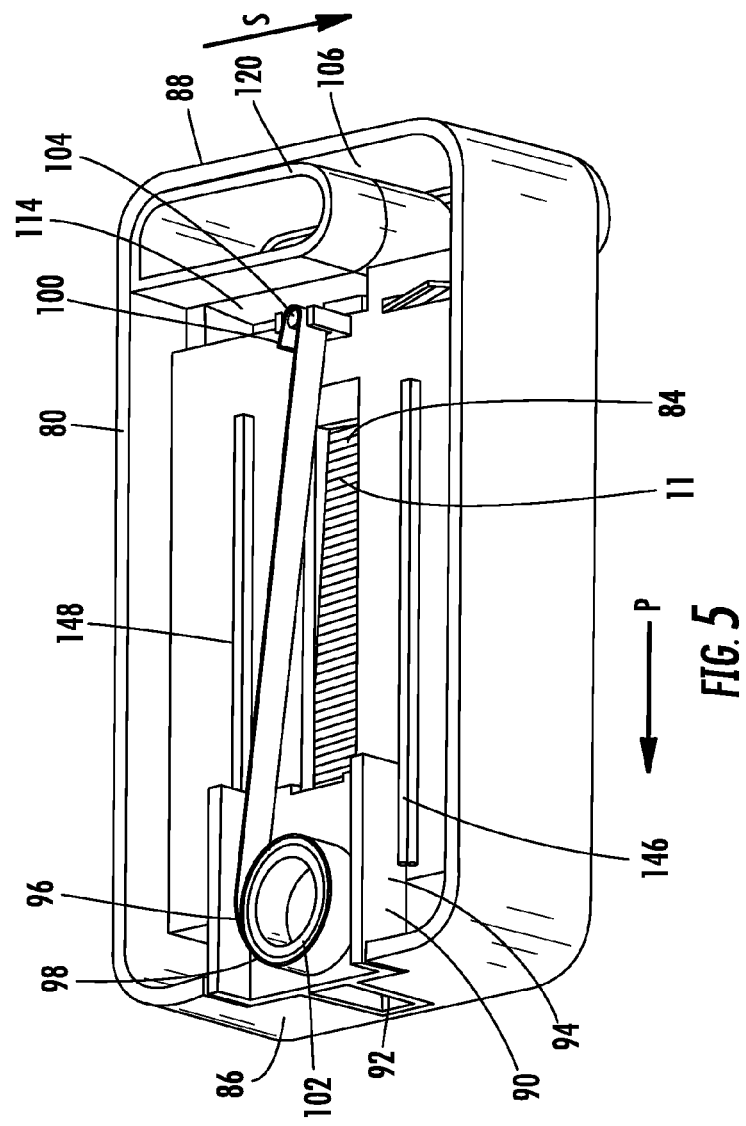
FIG. 5 is a bottom perspective view of the dispenser with the container removed, showing the cartridge and cartridge housing.

Referring to FIG. 5, a spring 96 is provided to bias the guide 90 in direction P. In the illustrated embodiment, the spring 96 is a clock spring having a first end 98 affixed to the guide 90 and a second end 100 affixed to a portion of the cartridge housing 80. The second end 100 is preferably affixed to a portion of the cartridge housing 80 proximate to the dispensing end 88 thereof, or at least further towards the dispensing end 88 of the cartridge housing 80 than the extension of the guide slot 84. Positioning the spring 96 in this manner enables it to draw the guide 90 in direction P, such that the guide rail 92 pushes the pusher bar 64, and in turn the stack 11 of strips 12, in direction P, towards the dispensing opening 54 of the cartridge 50. In the embodiment shown, the first end 98 of the spring 96 is looped around a protrusion 102 protruding from the bottom of the guide body 94, while the second end 100 extends around a catch 104 formed in the bottom surface of the cartridge housing 80.

Other ways of affixing the spring 96 to the guide 90 and cartridge housing 80 could be employed as well. In another embodiment, the first end 98 of the spring 96 could be affixed to the guide 90 and the second end 100 could be affixed to the container base 22. In another embodiment, the first end 98 of the spring 96 could be affixed to the guide 90 and the second end 100 could be affixed to the cartridge 50. In yet another embodiment, a different type of biasing element, such as a compression spring acting between the guide 90 and the container base side wall 30 at the feeding end thereof could be employed. In each of the embodiments, the spring 96 biases the guide 90 in direction P.

With reference to FIGS. 1-3 and 5, a slider 120 is provided for dispensing individual strips 12 from the stack 11. The slider 120 includes a body portion 122, an actuation portion 124, and a dispensing arm 126. The body portion 122 is housed within a channel 106 formed at the dispensing end of the cartridge housing 80. An access slot 108 is defined in a top wall 112 of the channel 106 and the actuation portion 124 of the slider 120 protrudes therethrough. As best seen in FIG. 5, the length of the slider 120, as measured in direction S, is less than the corresponding length of the channel 106. Likewise, the length of the actuation portion 124, as measured in direction S, is less than the corresponding length of the access slot 108. This arrangement enables the slider 120 to slide within the channel 106 and the actuation portion 124 to slide within the access slot 108 in direction S.

A side wall 116 of the channel 106 divides it from the recess 82 of the cartridge housing 80. This side wall 116 includes a slider arm slot 114. When the cartridge 50 is in place within the recess 82 of the cartridge housing 80, the slider arm slot 58 of the cartridge 50 aligns with the slider arm slot 114 of the channel side wall 116. The arm 126 of the slider 120 extends into the aligned slider arm slots 58, 114. Length of the arm 126, as measured in direction S, is less than the corresponding length of each of the slider arm slots 58, 114. This arrangement enables the arm 126 to slide within the slider arm slots 58, 114 in direction S.

To operate the dispenser, the actuation portion 124 of the slider 120 is slid in direction S from a first position as shown in FIG. 1 to a second position, as shown in FIG. 2, causing the arm 126 to slide within the aligned slider arm slots 58, 114 of the cartridge 50 and cartridge housing 80. The arm 126 is in contact with the contact corner 13 of one of the strips 12 located closest to the dispensing end 56 of the cartridge 50, and its movement in direction S causes the strip 12 to rotate in direction R. Due to this rotation, a dispensed end 18 of the dispensed strip 12 protrudes out from the dispensing opening 54 of the cartridge 50, so that it can be accessed and removed from the dispenser assembly 10 by a user. The clearance slot 60 permits passage of the end of the dispensed strip 12 opposite the dispensed end 18, so that rotation of the dispensed strip 12 is not blocked by the cartridge walls. After the strip 12 is removed from the stack 11, the biasing action of the spring 96 causes the guide 90, and in turn the pusher bar 64 and the stack 11 to move in direction "P" and close the gap created by the removal of the dispensed strip 12. The actuating portion 124 of the slider is returned to the position shown in FIG. 1 and the next strip 12 of the stack 11 can be dispensed in the same manner. Additionally, a spring may be incorporated to bias the slider 120 in the first position so that after the slider 120 has been moved from the first position and the user releases the actuator portion 124, the slider 120 may return to the first position. According to an embodiment, a spring, such as a helical spring, coil spring, extension spring, or constant force spring, among others may be placed between the slider 120 and a wall of the cartridge housing 80.

Preferably, the container 20 provides a sealed housing for the strips 12 when in the closed configuration. In this embodiment, the sealing mechanism may comprise a sealing material affixed to the dispensing cartridge 50. When the container 20 is in the closed configuration, an inner surface of the top wall 32 of the lid 24 contacts the sealing material to create a seal between the lid 24 and the cartridge 50. The sealing material could be any material known in the art for creating a seal between two structures, such as an elastomeric material. In one embodiment, the cartridge housing 50 is provided as a disposable component, including the sealing material, and the container 20 and possibly cartridge housing 80 are provided as reusable components. This embodiment has the advantage of ensuring that the sealing material is replaced periodically, to avoid compromise of the seal if and when the sealing material becomes worn. In another embodiment, the lid 24 could be provided with the sealing material on an inner surface of the top wall 32. When the lid 24 is closed on the base 22, the sealing material contacts the cartridge 50 and/or an upper edge of the base side wall 30 to produce a seal between the base 22 and the lid 24. In yet another embodiment, lid 24 could be positioned so that an inner surface of the lid side wall 34 comes into contact with an outer surface of the base side wall 30 when the lid 24 is closed on the base 22. An interference fit is formed between the lid side wall 34 and the base side wall 30 to form a seal. This type of seal could be combined with the use of an elastomeric material as described above. Other types of seals could be employed as well, such as the use of an o-ring surrounding the base side wall 30 or placed within the lid side wall 34.

Figure 6A:
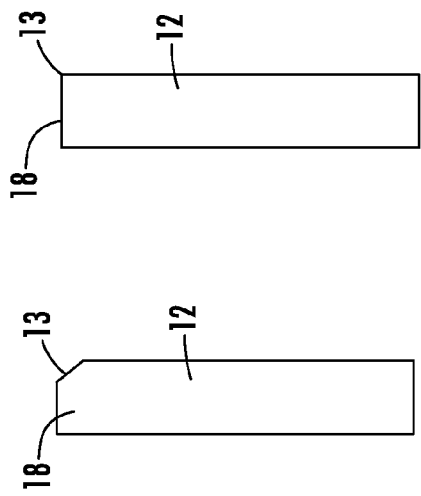
FIG. 6A shows an embodiment of a test strip for use with the dispenser of FIG. 1.
Figure 6B:
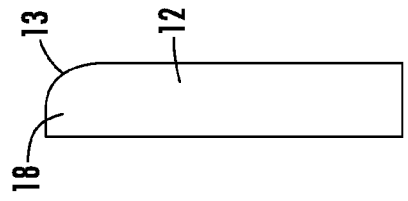
FIG. 6B shows a second embodiment of test strip for use with the dispenser of FIG. 1.
Figure 6C:
FIG. 6C shows a third embodiment of a test strip for use with the dispenser of FIG. 1.

Several embodiments of strips 12 for use with the dispenser assembly 10 are shown in FIGS. 6A-6C. FIG. 6B shows a conventional strip 12, having a generally rectangular shape. The corners of the strip form substantially right angles, including a contact corner 13 that is contacted by the slider arm 126 during dispensing. FIG. 6A shows a second embodiment of a strip 12 that can be used with the disclosed dispenser assembly 10. This strip 12 has a beveled contact corner 13, which may facilitate engagement of the slider arm 126 therewith to initiate dispensing of the strip. The strips shown in FIG. 3 have the configuration of that of FIG. 6A. FIG. 6C shows a third embodiment of a strip 12 that can be used with the disclosed dispenser assembly 10. This strip 12 has a rounded contact corner 13, which may further facilitate engagement of the slider 126 in a similar manner as that of the strip shown in FIG. 6A.

As mentioned above, in one embodiment, the container 20 is provided as a reusable component of the assembly and the cartridge 50 is provided as a disposable component. In this embodiment, the strips 12 and cartridge 50 could be provided as a unit, housed within a sealed packaging 70, shown in FIGS. 7A and 7B. Once the stack of strips 12 is exhausted, the empty cartridge 50 can be removed from the cartridge housing 80 within the container 20 and disposed of. A new cartridge 50 is then removed from the sealed packaging 70 and placed within the cartridge housing 80 within the container 20. The container dispenser assembly 10 then creates a new sealed environment for the strips 12 prior to dispensing and use. While FIGS. 7A and 7B show the cartridge 50 and strips 12 alone provided as a disposable unit, it should be understood that in other embodiments the cartridge housing 80 could be provided as a portion of the disposable unit as well. Alternatively, the cartridge housing 80 could be provided as a reusable component, along with the container 20.

Figure 8:
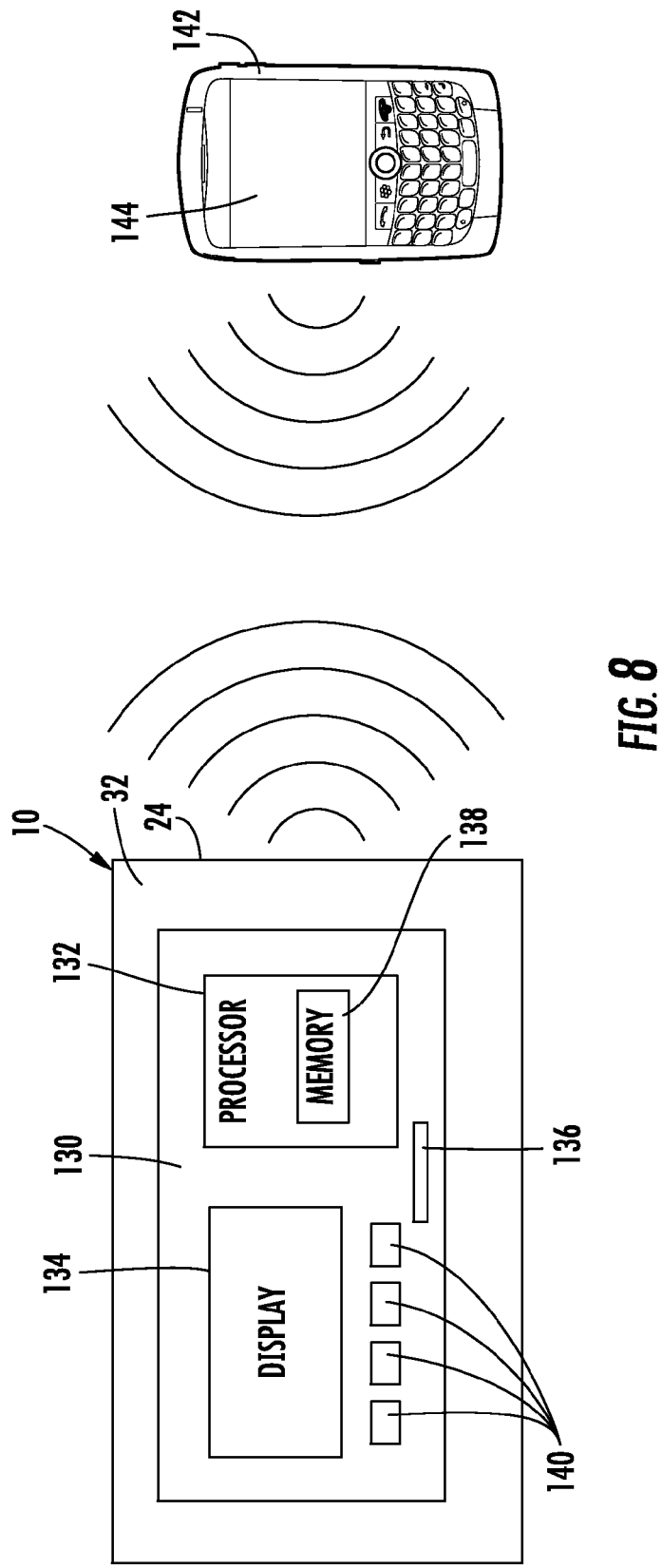
FIG. 8 is a top perspective view of a dispensing apparatus having interface electronics.

An embodiment of the dispenser assembly 10 having interface electronics 130 is shown in FIG. 8. In this embodiment, the electronics 130 are provided in the container 20, but in other embodiments the electronics 130 could be provided in other components of the assembly 10, such as the cartridge 50 or the cartridge housing 80. Incorporation of the electronics 130 in the container 20 portion of the assembly 10 can be particularly useful in embodiments where the container 20 is provided as a reusable component and the cartridge 50 and/or cartridge housing 80 are provided as disposable components. In the illustrated embodiment, the electronics 130 are incorporated into the lid 24, but could be incorporated into other portions of the container 20 as well. The electronics 130 preferably include a processor 132 and a display 134 that can be used to display information to a user of the assembly 10. For example, in one embodiment, the strips 12 housed by the assembly 10 could be blood diagnostic test strips 12, such as blood glucose test strips 12. In this embodiment, the electronics 130 could include a port 136 for receiving a test strip 12. The processor 132 of this embodiment is in communication with the port 136 and processes information pertaining to blood glucose values detected by the test strips 12. The display 134 then displays values pertaining to blood glucose values. The processor 132 could include a memory 138 for storing data, such as test values and the time and date on which they were obtained. The processor 132 could be configured to retrieve these values when commanded by a user, by for example, pressing one or more buttons 140 provided on the electronics 130, and the display 134 could be configured to then display the values.

The electronics could optionally be configured to communicate with an outside electronic device 142 capable of receiving and processing a signal therefrom. The outside device could be, for example, a computer, handheld wireless electronic device, or cellular phone. In this embodiment, the outside device 142 could include a display 144 and be configured to display information to the user in place of or along with the display 134 of the dispenser assembly 10. The display 134 of the assembly 10 could optionally be configured to only display only limited information, or could be eliminated in its entirety. Reducing the size of or eliminating the display 134 has the advantage of reducing the energy consumed by the electronics 130. The outside electronic device 142 can be capable of permitting user interaction by way of a program or application, which could be for example provided with the assembly 10 or available via the internet.

Another embodiment of a dispenser assembly 200 is shown in FIGS. 9-18. The dispenser assembly 200 includes a container 210 having a lid 202 that is pivotally attached to a base 204, such as by a hinge 26. The base 204 includes sidewalls 210 and a bottom wall 203 that generally define an interior area 205. The interior area 205 is sized to receive the insertion of an attachment member 214. The attachment member 214 may be secured to the base 204, such as, for example, through a snap-fit, mechanical fastener, adhesive, or welding. The attachment member 214 has a first end 216 at the feeding end, and a second end 218 at the dispensing end. The first end 216 is configured for engagement with at least a portion of a guide 220. Moreover, the first end 216 includes a portion of a guide slot 222, the guide slot 222 extending along at least a portion of the attachment member 214. The guide slot 222 is configured to guide the movement of a guide 220, and particularly the rail 224 that extends from a guide body 226, along the attachment member 214.

Figure 14:
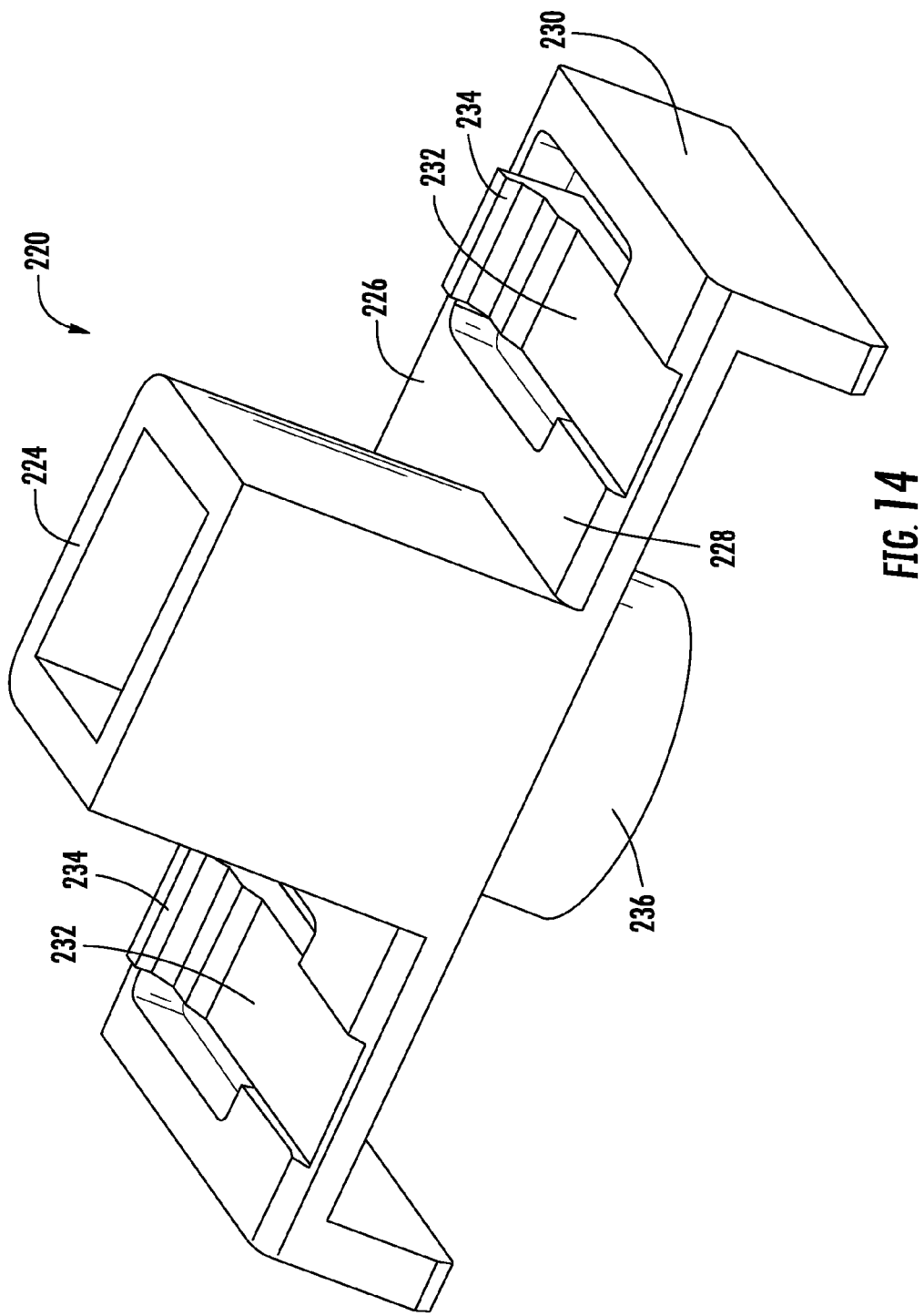
FIG. 14 is a rear side perspective view of a guide according to an embodiment of the present invention.
Figure 15:
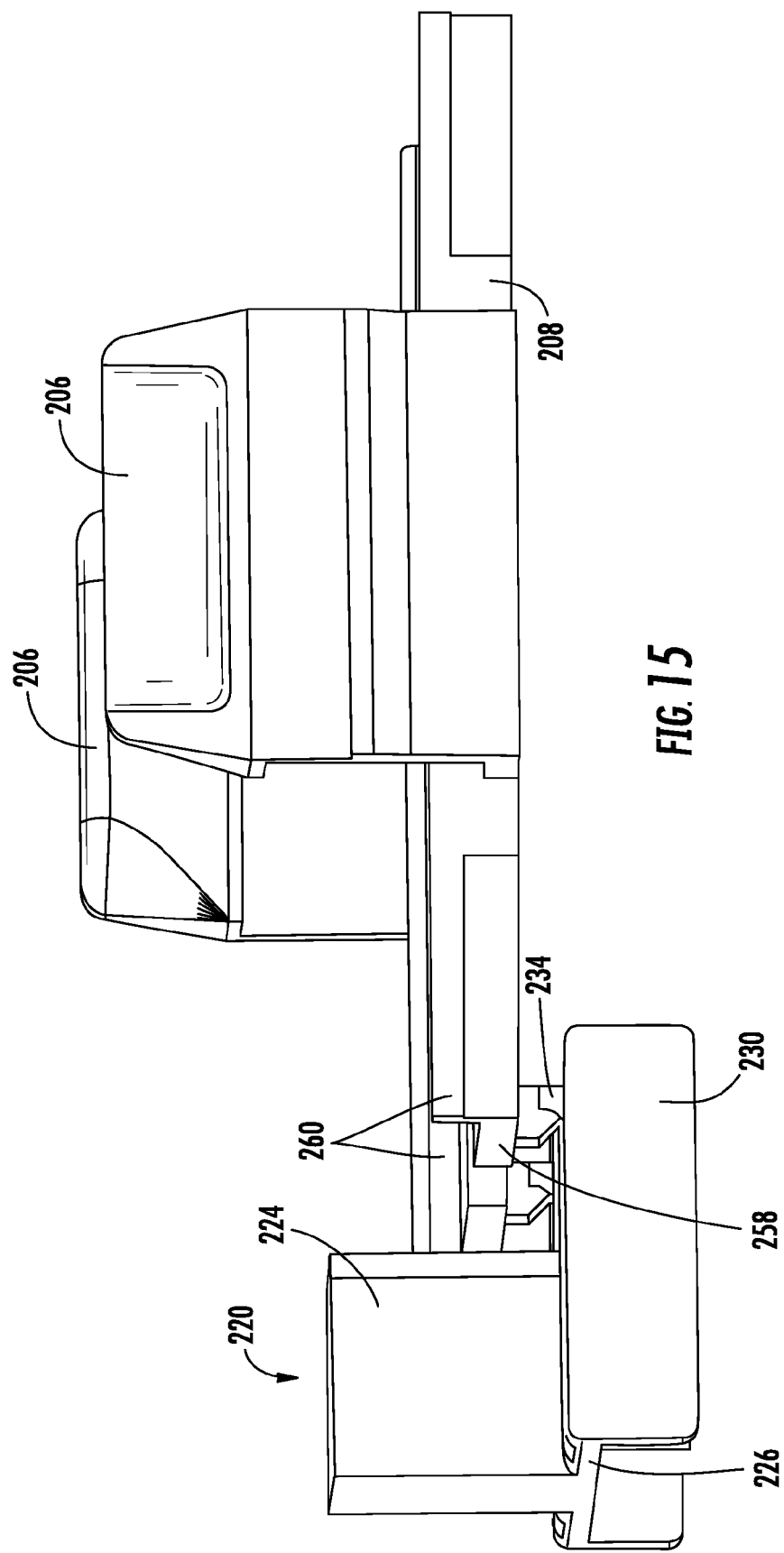
FIG. 15 is a side perspective view of a guide and a cartridge according to an embodiment of the invention.

FIG. 14 illustrates a guide 220 according to an embodiment of the present invention. As shown, the guide body 226 includes a first wall 228 and a second wall 230, the second wall 230 extending downwardly from the first wall 228. The first wall 228 may include at least one latch 232 that includes a hook. 234. At least a portion of the latch 232 is separated from the first wall 228 to allow the latch 232 to move from a first, rest position to a second, depressed position, and vice versa, as discussed below. Additionally, according to an embodiment, a protrusion 236 may also downwardly extend from the first wall 228, the protrusion 236 being configured to secure a first end 240 of a spring 238 to the guide 220. The second end 242 of the spring 238 may be connected to the base 204 or the attachment member 214, such as by the catch 244 shown in FIGS. 13 and 17.

Figure 10:
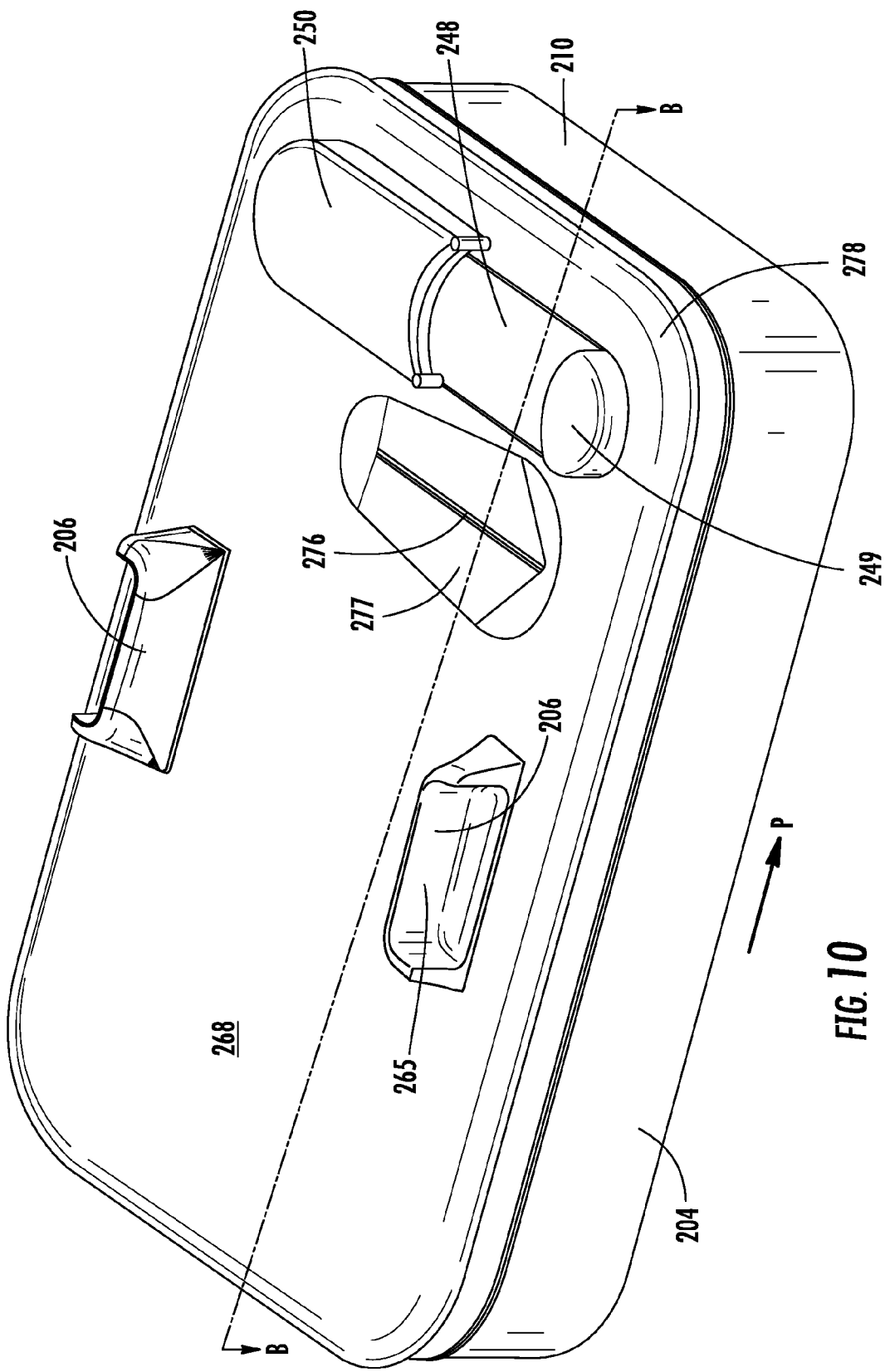
FIG. 10 is a top perspective view of the dispenser of FIG. 9 (shown without the lid) having the slider in a first, or starting, position.
Figure 11:
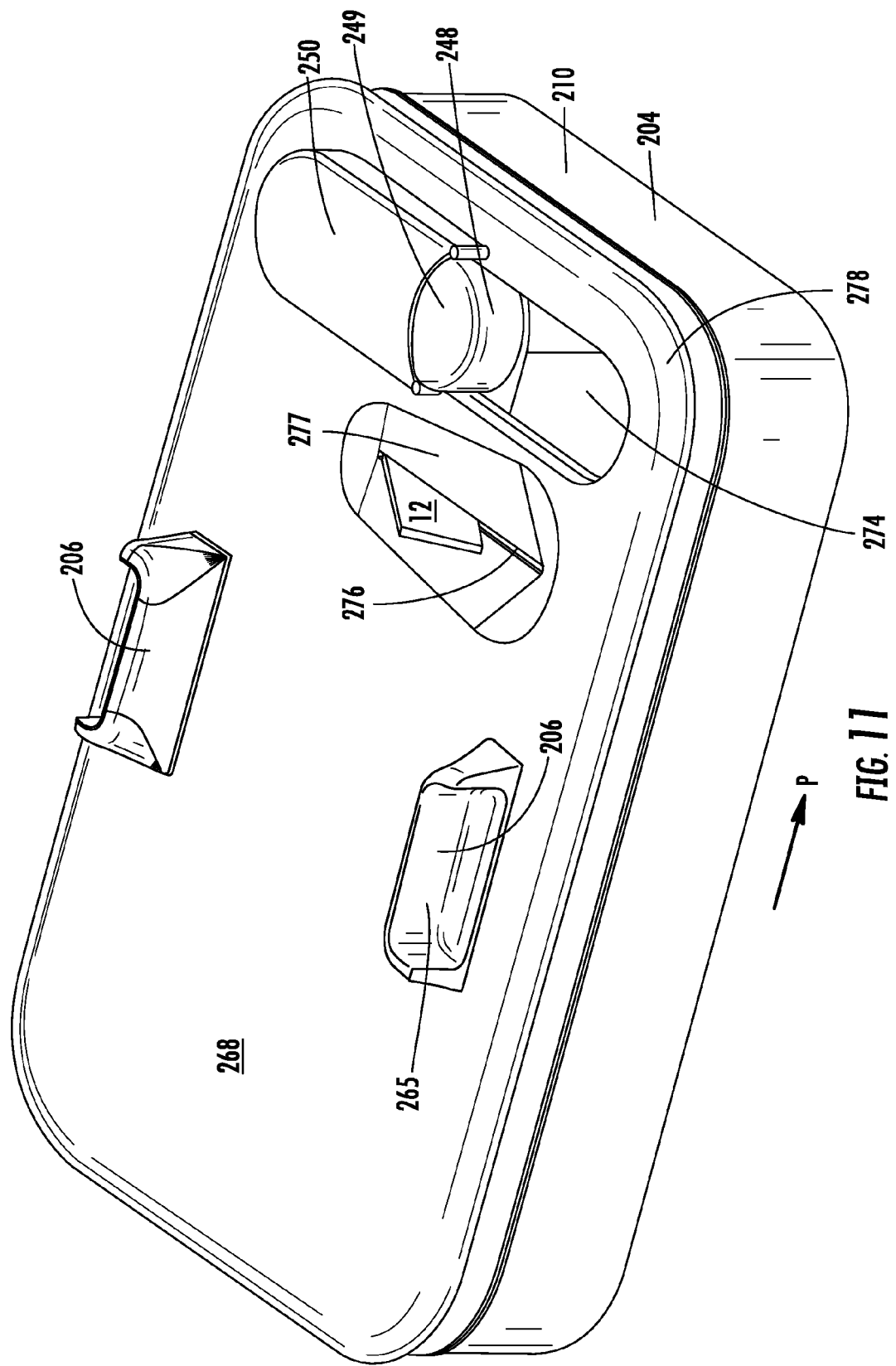
FIG. 11 is a top perspective view of the dispenser of FIG. 9 (shown without the lid) having the slider in a second, or dispensing, position.
Figure 12:
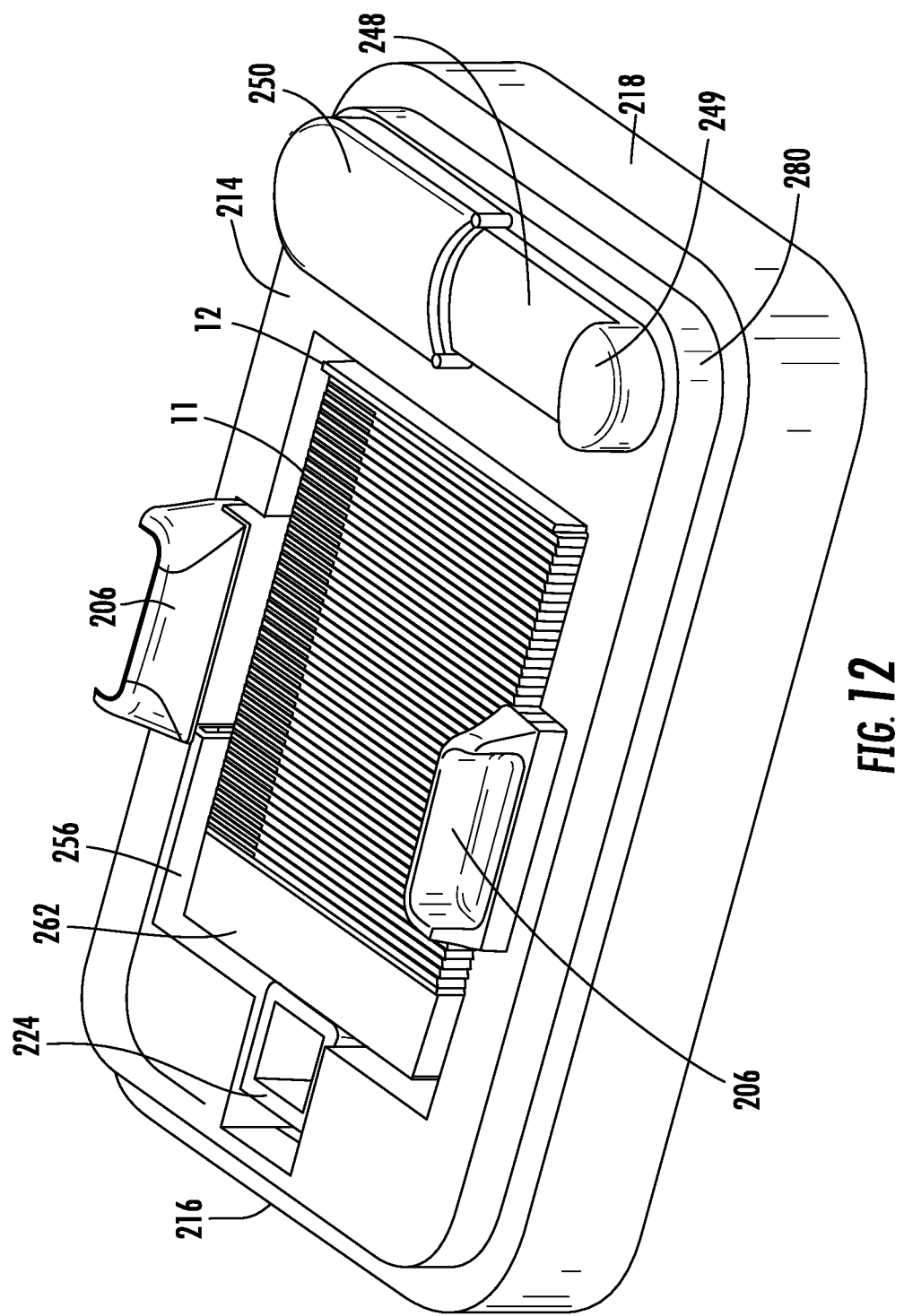
FIG. 12 is a top perspective view of an cartridge, guide, and slider assembled in an attachment member according to an embodiment of the invention.
Figure 13:
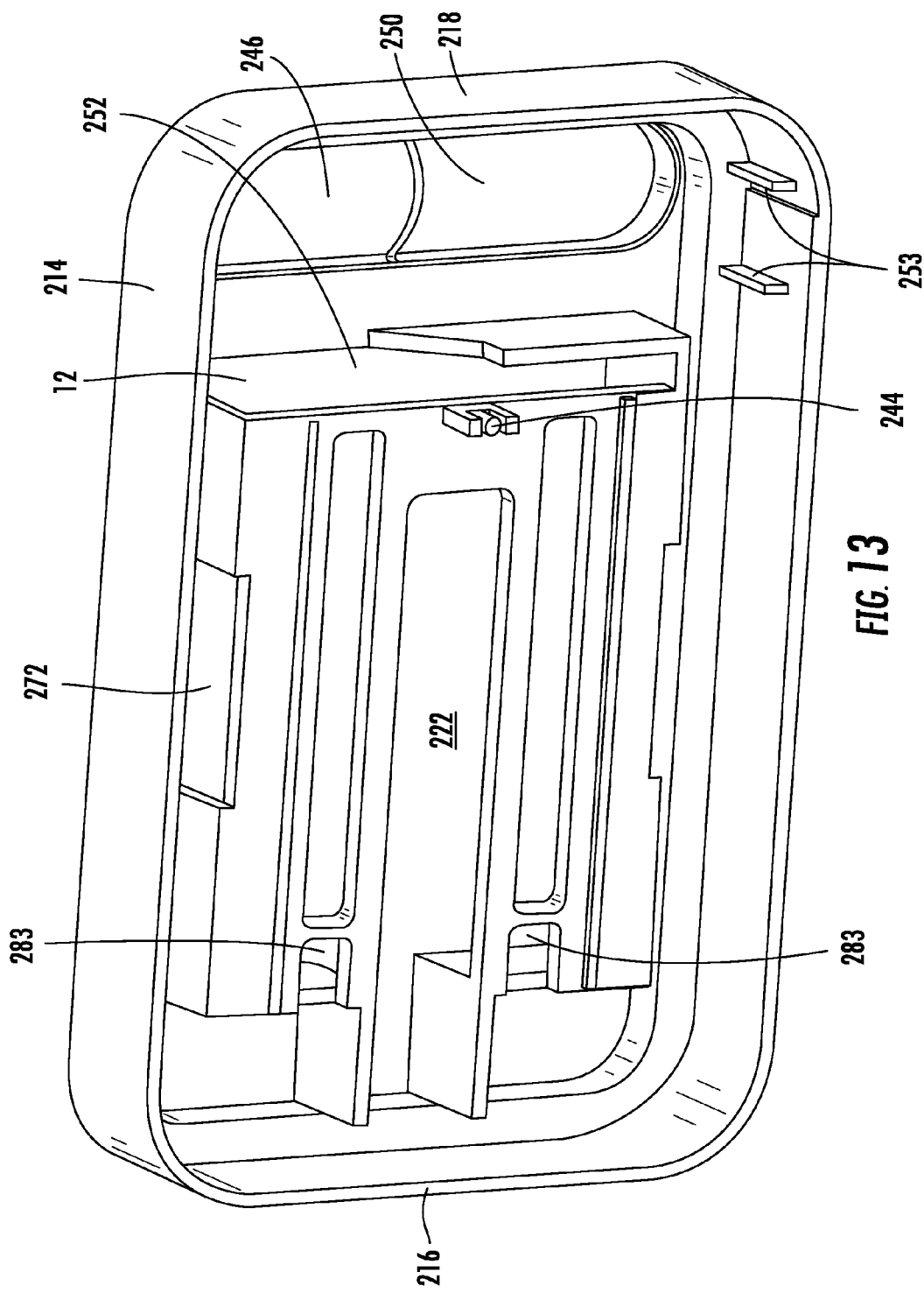
FIG. 13 is a bottom perspective view of an attachment member according to an embodiment of the invention.

The second end 218 of the attachment member 214 includes a channel 246 along which a slider 248 may move from a first position, as shown in FIG. 10, to a second position, as shown in FIG. 11, and vide versa. At least a portion of the channel 246 may be covered by, or terminate at, a top wall 250. The top wall 250 and/or the channel 246 may be configured to restrict the distance that the slider 248 may be displaced when the slider 248 is moved to the second position. Additionally, the attachment member 214 includes a slider arm slot 252 through which the slider arm 254 of the slider 248 may extend and engage a strip 12 when the slider 248 is being moved from the first position to the second position.

The attachment member 214 also includes an interior region 256 that is configured to receive the placement of at least a portion of a cartridge 208. The cartridge 208 includes at least one grip 206 that extends from a bottom portion 258 of the cartridge 208. The cartridge 208 is configured to receive the placement of a product, such as a stack of strips 11. The strips 11 may be placed on at least a portion of the bottom portion 258 of the cartridge 208. According to an embodiment, sidewalls 260 may at least partially extend from the bottom portion 258 to assist in securing the placement, and/or guiding the displacement, of the stack of strips 11 along the cartridge 208 as individual strips 12 are dispensed from the dispenser assembly 200.

Similar to the dispenser assembly 10 previously discussed, a pusher bar 262 may be placed within the interior region 256, and more specifically on the bottom portion 258 of the cartridge 208 at the feeder end of the stack of strips 11. During use, the spring 238 exerts a force on the guide 220 in the general direction "P" (as shown in FIGS. 10 and 11), causing the rail 224 to engage the pusher bar 262 so that the stack of strips 11 is pushed toward the dispensing end of the assembly 200.

Figure 9:
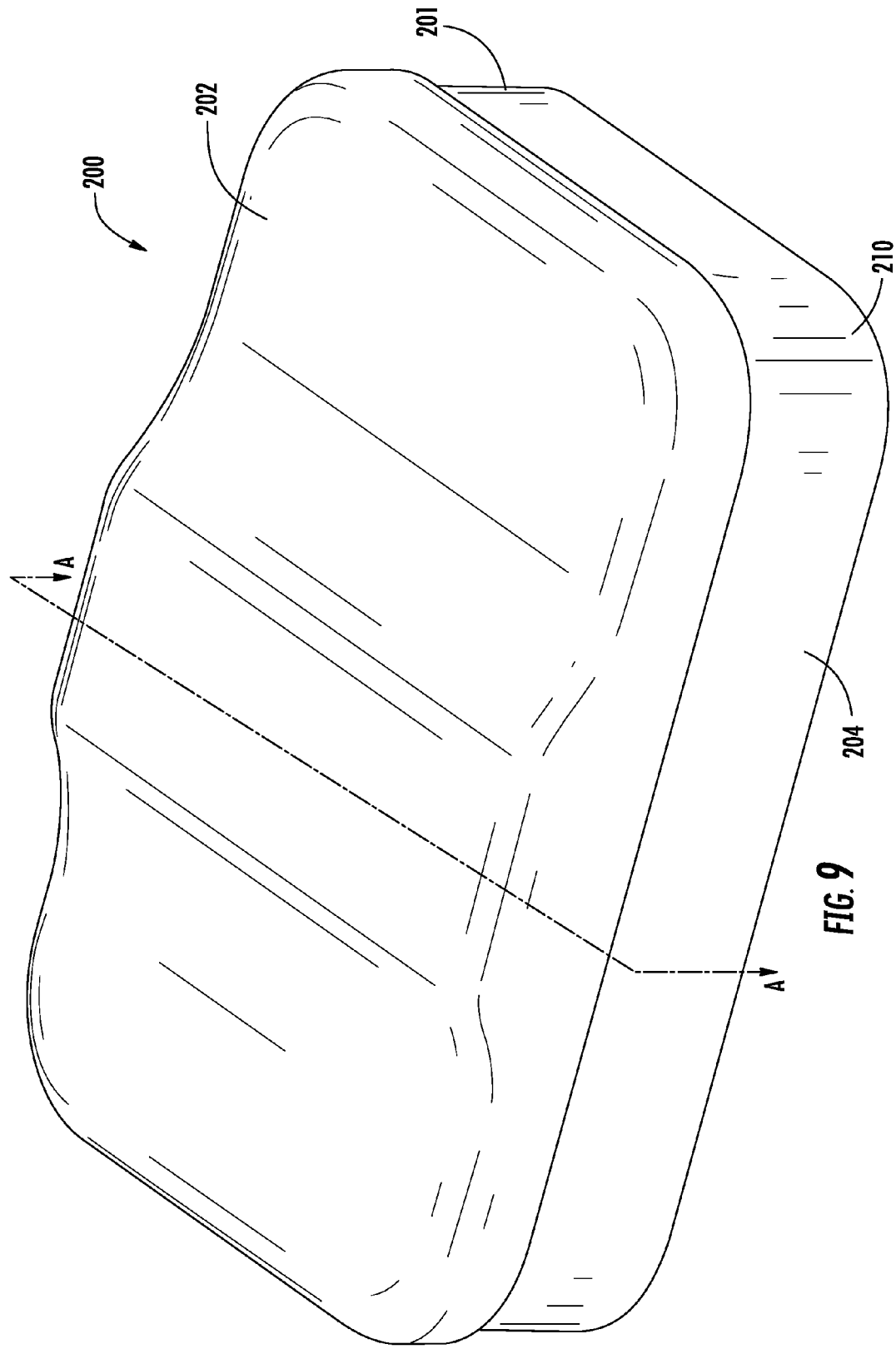
FIG. 9 is a top perspective view of an embodiment of a dispenser in a closed position.

According to an embodiment, the cartridge 208 includes grips 206 that are configured to engage the attachment member 214 so as to secure the cartridge 208 to the dispenser assembly 200. For example, according to the embodiment illustrated in FIG. 16a, the grips 206 include a grip protrusion 264 or latch that mates with a protrusion 266 or recess in the attachment member 214 or base 204, or vice versa. In the embodiment shown in FIG. 16a, when the cartridge 208 is inserted into the interior region 256, the grips 206 are inwardly displaced, bent, deformed, or depressed until the grip protrusion 264 matingly engages, and is secured to, the attachment member 214 or base 204. When the cartridge 208 is to be removed from the dispenser assembly 200, a user applies a force on the grip interface 265 to inwardly displace at least a portion of the grips 206 so that the grip protrusion 264 disengages from the protrusion 266 or recess in the attachment member 214 or base 204, or vice versa, thereby removing the interference between the cartridge 208 and the attachment member 214 or base 204 so that the cartridge 208 may be removed from the interior region 256. According to certain embodiments, the grip interface 265 may be a recessed portion of the grip 265 that assists in the ability of the user to inwardly press on the grips 206 and also grab onto the grips 206 so as to lift the cartridge 208 away from at least the container 201. Additionally, as the grips 206 may extend away from, and above, the base 204, according to an embodiment of the invention the lid 202 may have a contoured shape, such as a wave-shape as shown in FIG. 9, among other shapes and configurations, to accommodate the shape of the grips 206.

Figure 16A:
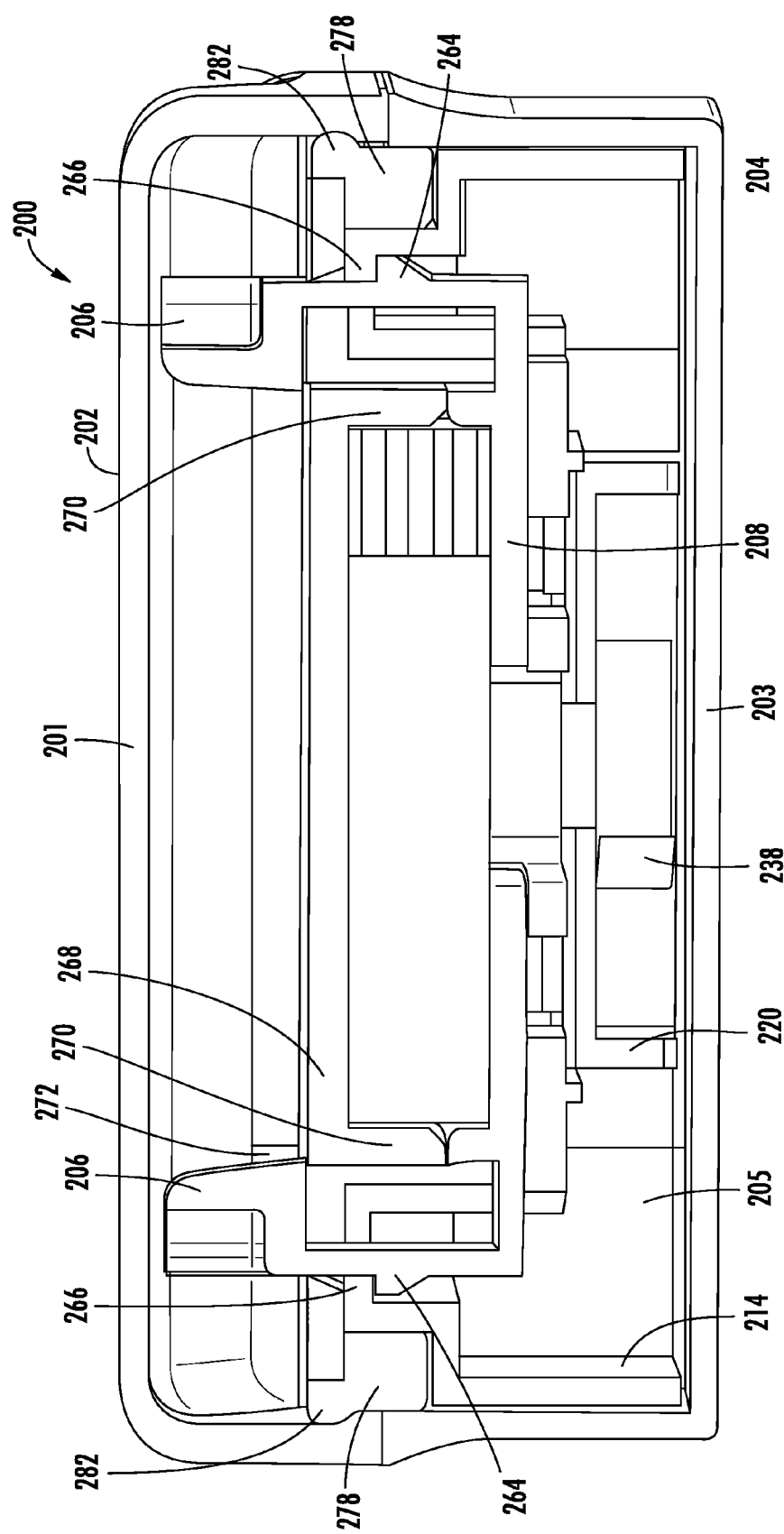
FIG. 16a is a cross sectional view of the dispenser taken along section A-A in FIG. 9.

The cartridge 208 may also include a cover 268 that covers the product contained within the cartridge 208. As shown in FIG. 16a, according to an embodiment, the cover 208 may include an inner sidewall 270 that extends toward the sidewall 260 of the cartridge 208 so as to further define a product containing space for the stack of strips 11, and which may also assist in guiding the displacement of the stack of strips 11 as the strips 11 move towards the dispensing end of the dispenser assembly 200 as individual strips 12 are dispensed.

The cover 268 may also include one or more orifices 272 that are configured to accommodate the protrusion of the grips 206 out from the cover 268 so that a user may have access to the grips 206. The orifices 272 may be sized to accommodate the displacement of the grips 206 as the cartridge 208 is being inserted into, and removed from, the attachment member 214 and/or base 204. The cover 268 may also include a slot 274 that is configured for the slideable movement of the slider 248 from the first position to the second position, as well as to accommodate the protrusion of the top wall 250. Additionally, the cover 268 includes a dispensing opening 276 through which individual strips 12 may be dispensed from the dispenser assembly 200. As shown in FIGS. 10 and 11, according to certain embodiments, the area adjacent to the dispenser opening 276 may have a recessed area 277 or indentation so as to assist the ease with which a user may grip a strip 12 that is being dispensed through the dispensing opening 276.

Figure 16B:
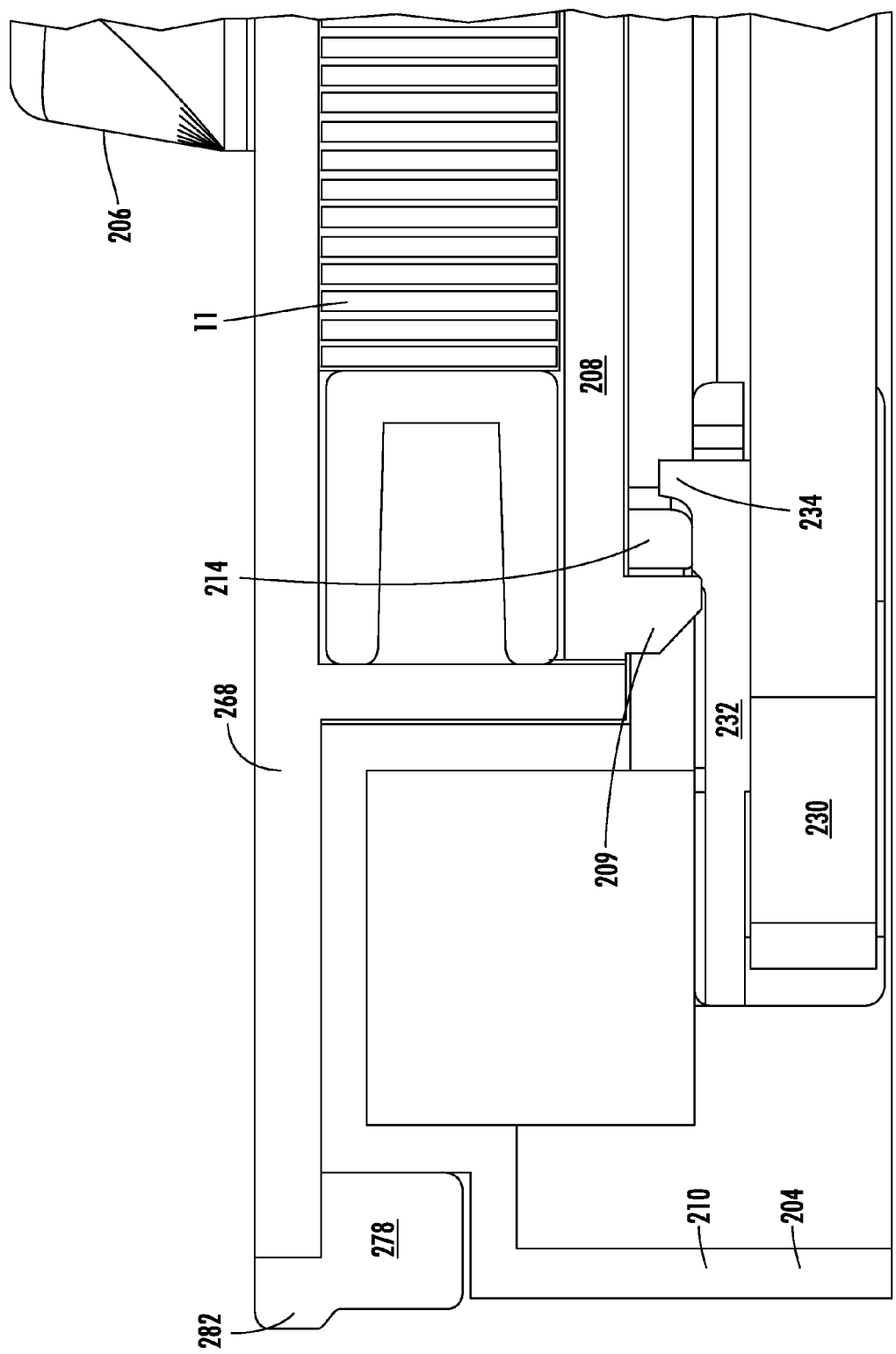
FIG. 16b is a cross sectional view of a dispenser taken along a portion of the section B-B in FIG. 10.
Figure 17:
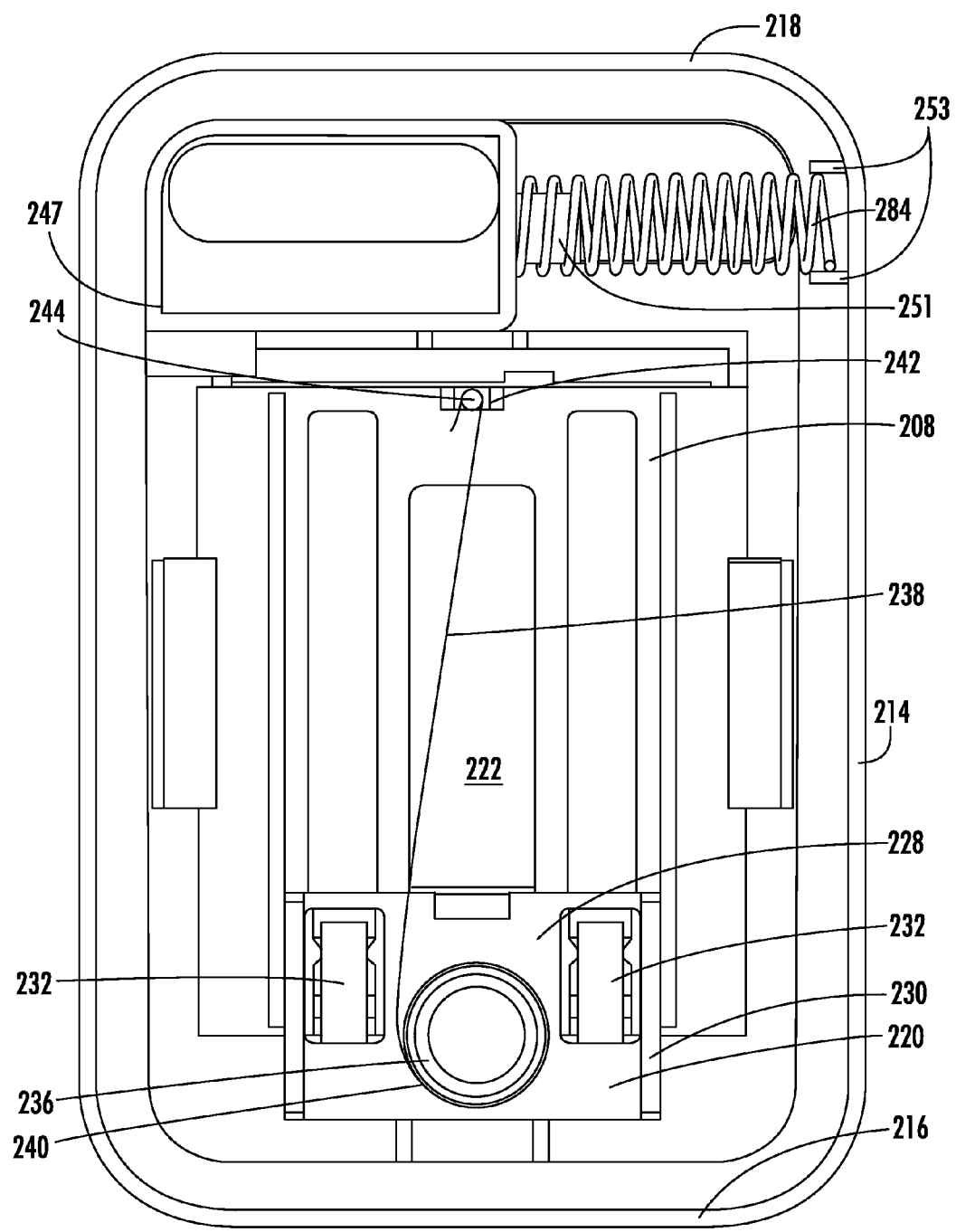
FIG. 17 is a bottom view of a cartridge, guide, and slider assembled in an attachment member according to an embodiment of the invention.
Figure 18:
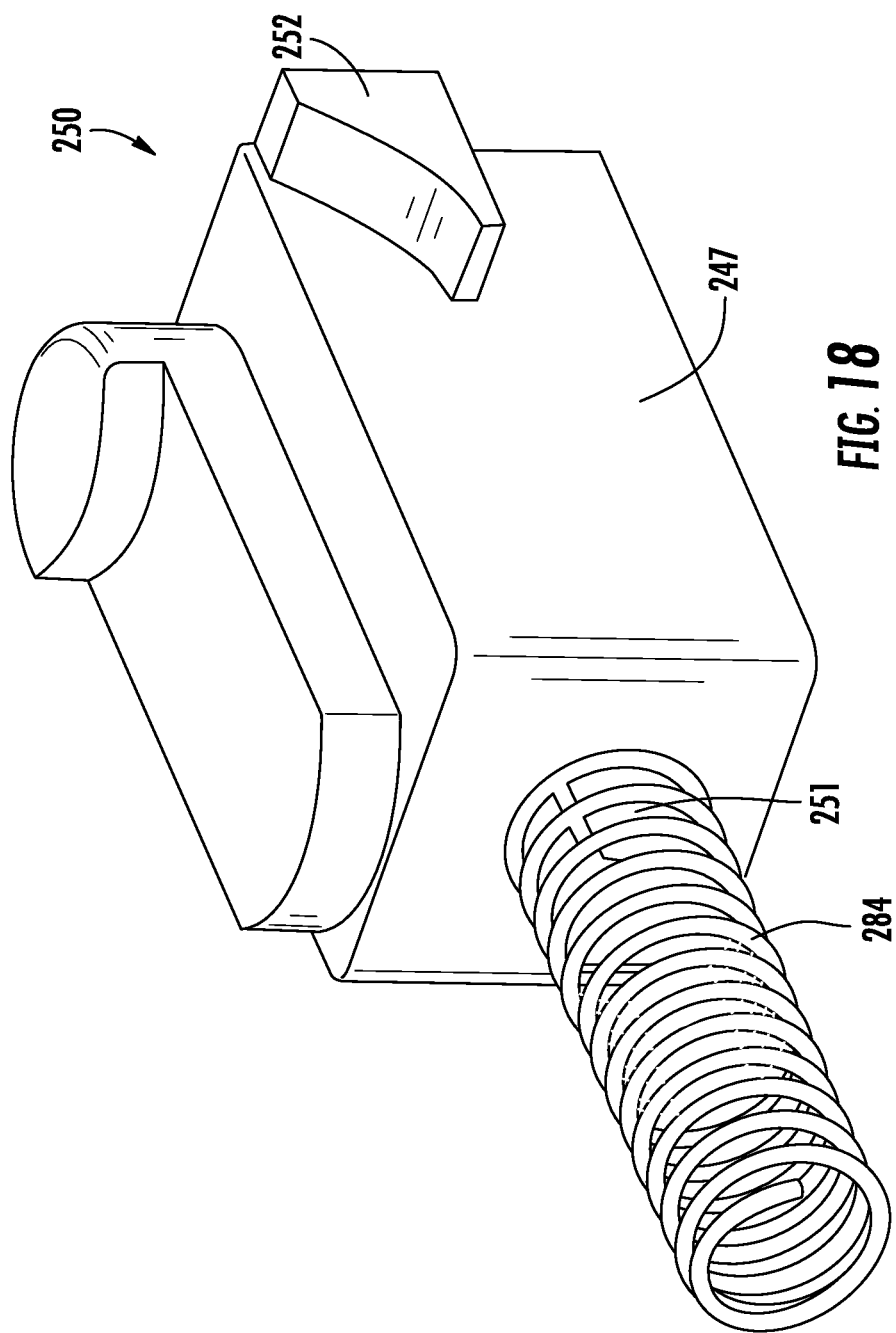
FIG. 18 is a side perspective view of a slider according to an embodiment of the invention.

According to an embodiment, the cover 268 may be attached to a seal 278 such as, for example, an elastomeric seal 278 that is positioned around an outer peripheral surface of the cover 268. According to such embodiments, the seal 278 may securely fit around an upper wall 280 of the attachment member 214, as shown in FIG. 16a, or between the attachment member 214 and the base 204. However, according to certain embodiments, the seal 278 may be placed in a variety of different locations, or have multiple seals in different locations. For example, according to certain embodiments, a seal may extend upwardly from the cover 268 and abut the top wall 32 of the lid 202. Additionally, the seal 278 may include an upper lip 282 that mates with, or engages the lid 202 when the lid is in a closed position (as shown in FIGS. 9, 16a, and 16b) to form a seal the prevents the ingress of moisture into the dispenser assembly 200. According to embodiments in which the seal 278 is an elastomeric material, the seal 278 may be deformable so as to allow the lid 202 to be moved to and from an open position and still engage the lid 202 to form a seal when the lid 202 is in the closed position. Further, according to certain embodiments, the seal 278 may assist in securing the cover 268 to the cartridge 208, attachment member 214, and/or the base 204. Alternatively, or additionally, the cover 268 may be secured to the cartridge 208, such as by an adhesive, mechanical fastener, interference fit, snap fit, or weld, among others.

According to one embodiment, the cartridge 208, pusher bar 262, cover 268, and seal 278 may be either individually or collectively part of a removable and/or disposable unit. According to such an embodiment, before the cartridge 208 is inserted into the dispenser assembly 200, the guide 220 may be pulled toward the first end, or feeding end, of the dispenser assembly 200. Additionally, according to certain embodiments, the guide 220 may be pulled toward the feeding end until the at least one latch 232, and particularly, the hook 234, engages with the attachment member 214, such as engages a recess 283 or protrusion in the attachment member 214, so as to lock the position of the guide 220. With the guide 220 in the locked position, a new or re-filled the cartridge 208 may then be inserted into the attachment member 214. More specifically, a refilled or replacement cartridge 208 inserted into the attachment member 214 may include a stack of strips 11 and a pusher base 204, and be covered by the same or a replacement cover 268 and a seal 278. However, according to other embodiments, one or more of these items may be separately replaced in the assembly 200. The cartridge 208 is inserted until the grip protrusion 264 lockingly mates with the protrusions 266 of the attachment member 214 or base 204, or vice versa. As shown in FIG. 16b, according to certain embodiments, the cartridge 208 includes a cartridge hook 209 or protrusion. According to such embodiment, when a reused or replacement cartridge 208 is being inserted or positioned in the recess area 277 of the attachment member 214, the cartridge hook 209 pushes the latch 232 downward so as to disengage a locking engagement between the guide 220 and the attachment member 214. The latch 232 may then, under the force exerted by the spring 238, move from the locked position and/or resume pressing against the pusher bar 262. Alternatively, once the cartridge 208 has been secured, the guide 220 may be depressed so as to disengage the hook 234 from the recess 283 in the attachment member 214, which causes the spring 238 to again pull the guide 220 toward the dispensing end.

Product may be dispensed from the dispenser assembly 200 in a manner similar to that discussed above with respect to the dispenser assembly 10 shown FIGS. 1-8. More specifically, with the lid 202 in an opened position, the user may displace the slider 248 from a first position to a second position. As the user displaces the slider 248 by pushing or pulling on the actuator portion 249 of the slider body 247, the slider 248 moves along the channel 246 while the slider arm 254 slides through a slider arm slot 252 in the attachment member 214 and engages an individual strip 12, such as engaging a lower corner of the strip 12. As previously mentioned, the contour of the slider arm 254, as well as the location of where on the strip 12 the slider arm 254 contacts, causes the strip 12 to rotate or pivot so that a portion of the strip 12 protrudes through the dispensing opening 276.

After the user releases the slider 248, a spring 284 biases the slider 248 back to the first position. As shown at least in FIG. 18, the slider body 247 has a protrusion 251 about which a first end of the spring 284 may engage, while a second end of the spring may be secured to, or engages, the attachment member 214 at or between a bracket 253. Additionally, after a strip 12 has been dispensed, the spring 238 biases the guide 220 toward the dispensing end, with the rail 224 of the guide 220 thereby pushing the pusher bar 262, and thus the remaining strips 11, toward the dispensing opening 276. As strips 12 are individually dispensed, the displacement of the rail 224 of the guide 220 will be guided by the guide slot 222 toward the dispensing end. When a user decides to remove the cartridge 208, such as, for example, after all the strips 12 have been dispensed, the user may inwardly depress the grips 206 so that the grip protrusions 264 disengage the mating protrusions 266 or recesses of the attachment member 214 or base 204. According to an embodiment, the user may then insert another replacement or refilled cartridge 208. Further, according to certain embodiments, rather than removing the cartridge 208, the user may remove the cover 268 so as to gain access to interior region 258 of the attachment member 214, whereby the user may displace the guide 220 and pusher bar 262 toward the feeding end before inserting additional strips 12 or stacks of strips 11. Again, according to such an embodiment, the user may lock the position of the guide 220 through the use of the latch 232 before refilling the cartridge with a strip 12 or a stack of strips 11.

Figure 19:
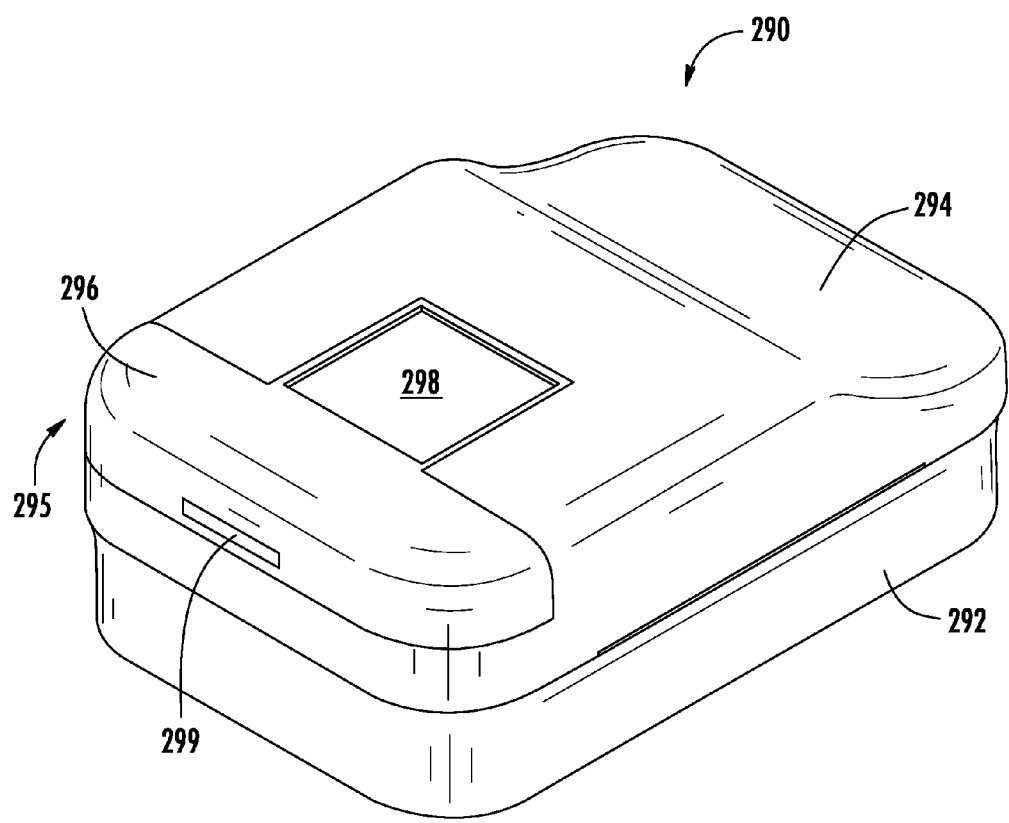
FIG. 19 is a top perspective view of a dispensing apparatus having a removable interface electronics.
Figure 20:
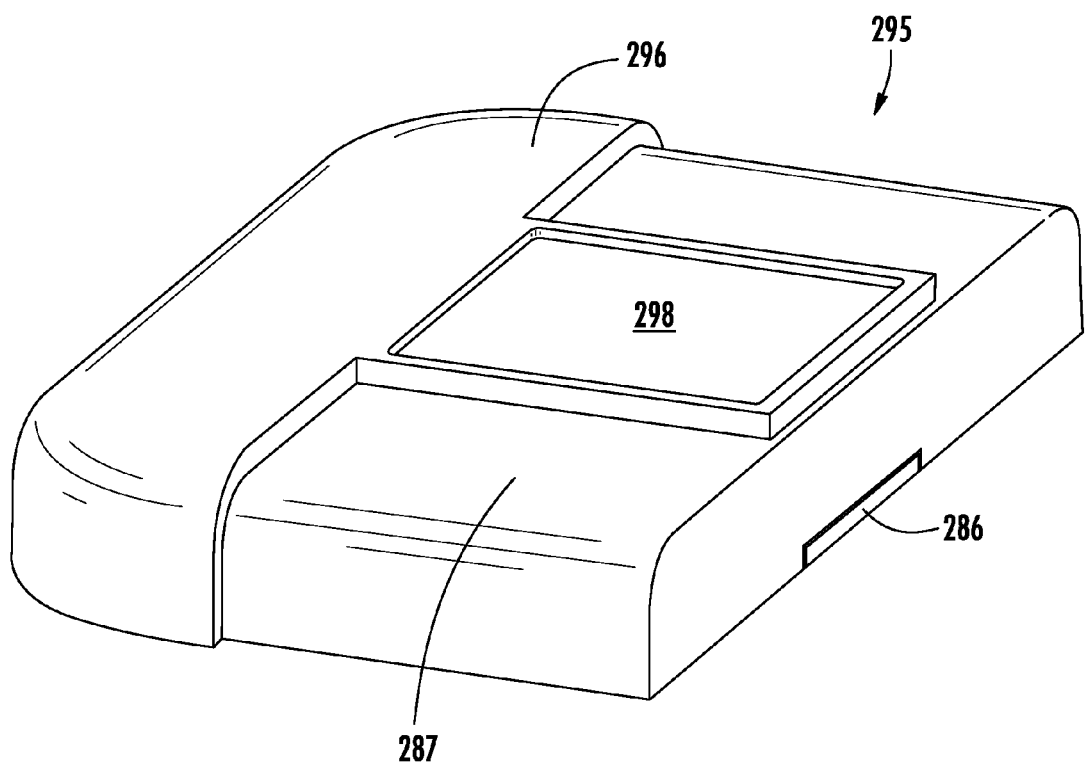
FIG. 20 is a perspective view of the interface electronics shown in FIG. 19.
Figure 21:
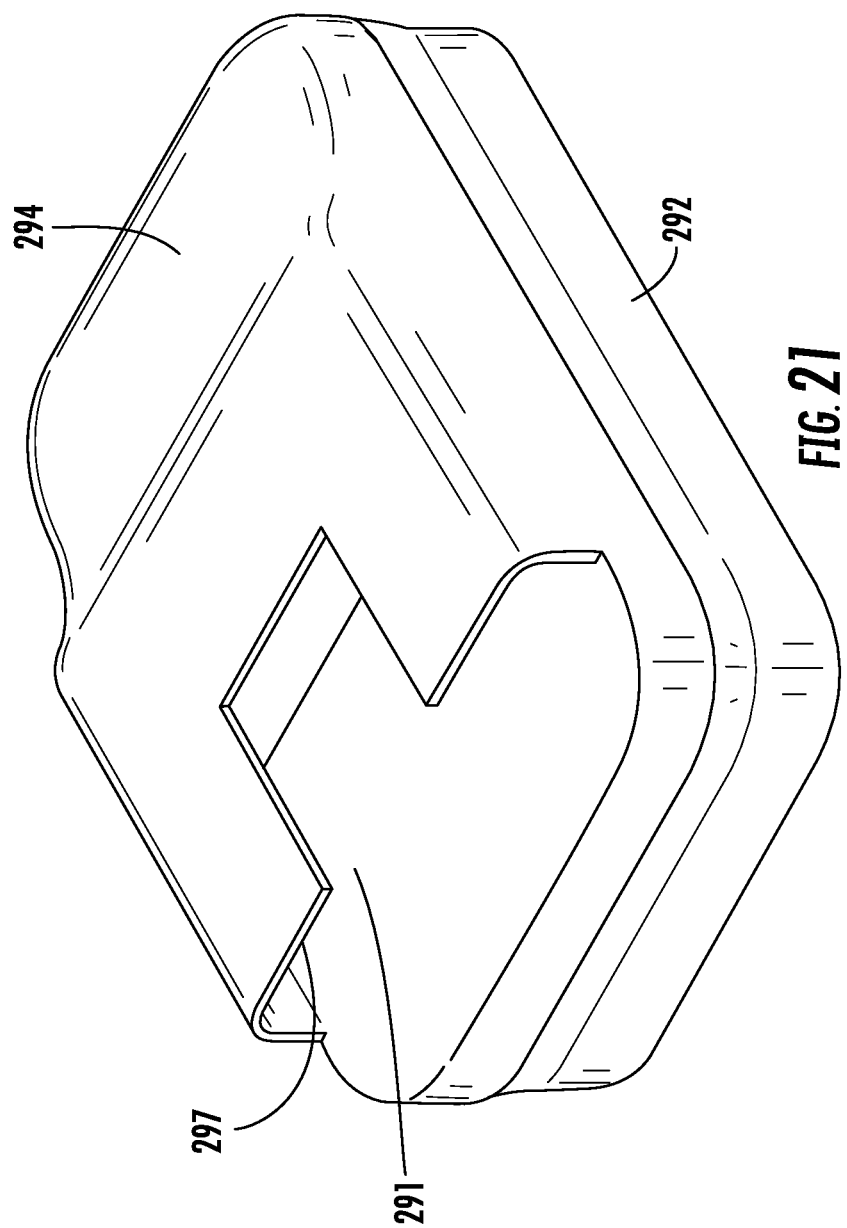
FIG. 21 is a perspective view of the interface electronics removed from the dispensing apparatus shown in FIG. 19.

FIGS. 19-21 illustrate a dispensing assembly 290 similar to the dispensing assemblies 10, 200 previously discussed but including a removable interface electronics 295. For example, as shown, the lid 294 may include a pocket 291 that is configured to receive the removable insertion of the electronics housing 296 of the interface electronics 295. The electronics housing 296 may be removably secured in the pocket 291, such as by an interference or press fit between a recessed surface 287 and an interior wall 297 of the pocket 291, or depressible levers or buttons that protrude from the electronics housing 296 and through apertures in the pocket 291, among others forms of removable attachment. The interface electronics 295 may operate similar to the interface electronics 140 previously discussed with respect to FIG. 8, and include a processor 132, a display 298, memory 138, and buttons 140. Additionally, similar to the interface electronics 130 discussed with respect to FIG. 8, according to certain embodiments, the display 298 may be part of an outside device 142, such as a personal digital assistant, mobile phone, or portable music device, among others. Further, the electronics housing 296 may also include a port 299 similar to the port 136 discussed with respect to FIG. 8, such as a port 296 that is configured to receive the insertion of a glucose strip, among others.

The interface electronics 140, 295 may include an internal or removable power source, such as an internal battery, among others, that may, or may not be, rechargeable. For example, as shown in FIG. 20, according to certain embodiments, the electronics housing 296 may include a connector 286 or power inlet that is configured to receive, or mate, with an adapter that is operably connected to a power source, such as an electrical wall outlet or computer, among others. This connector 286 may also allow information to be downloaded from and/or uploaded to the processer 132 or memory 134.

Figure 22:
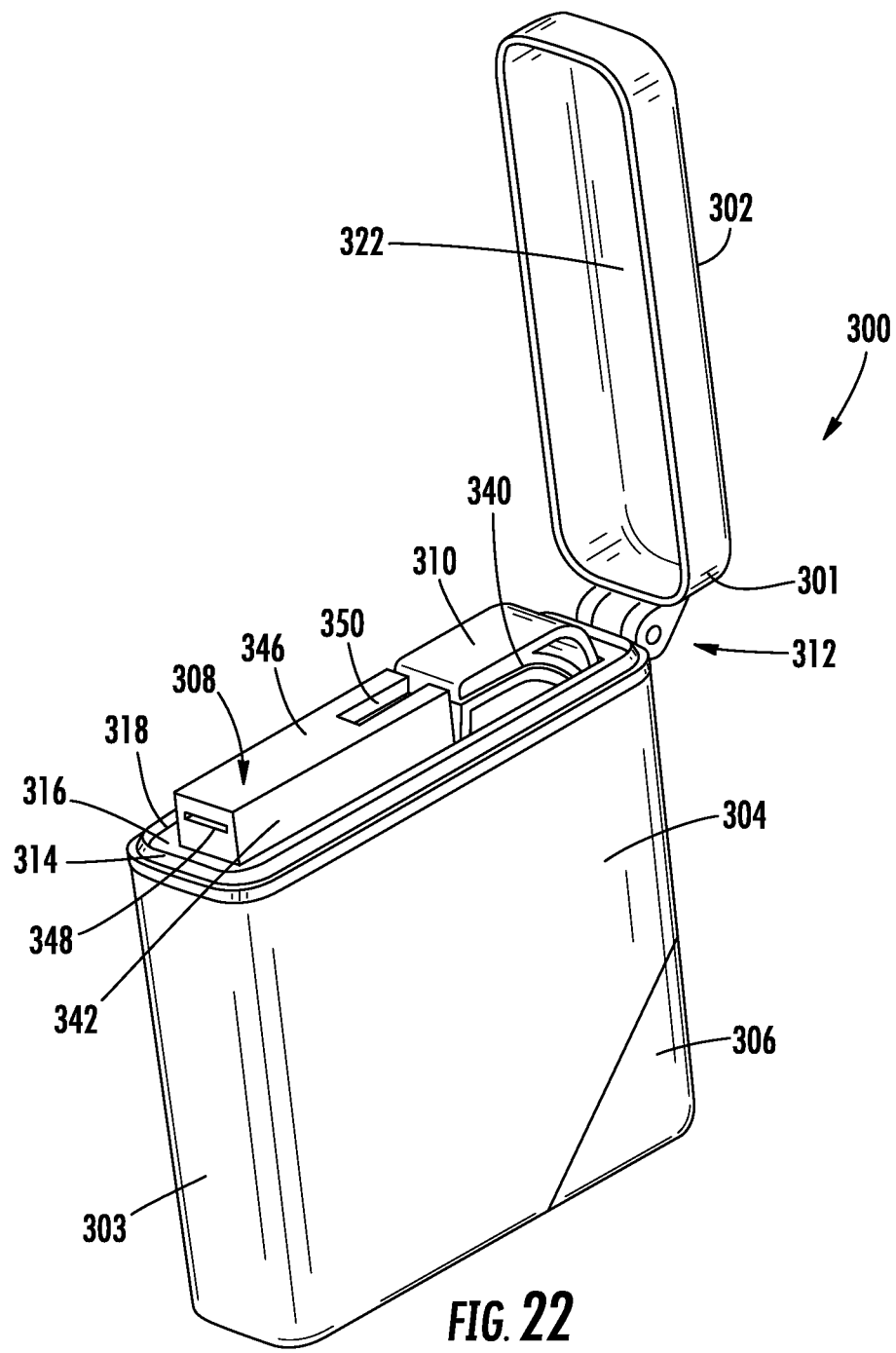
FIG. 22 is a side perspective view of an embodiment of a dispenser in an opened position.
Figure 23:
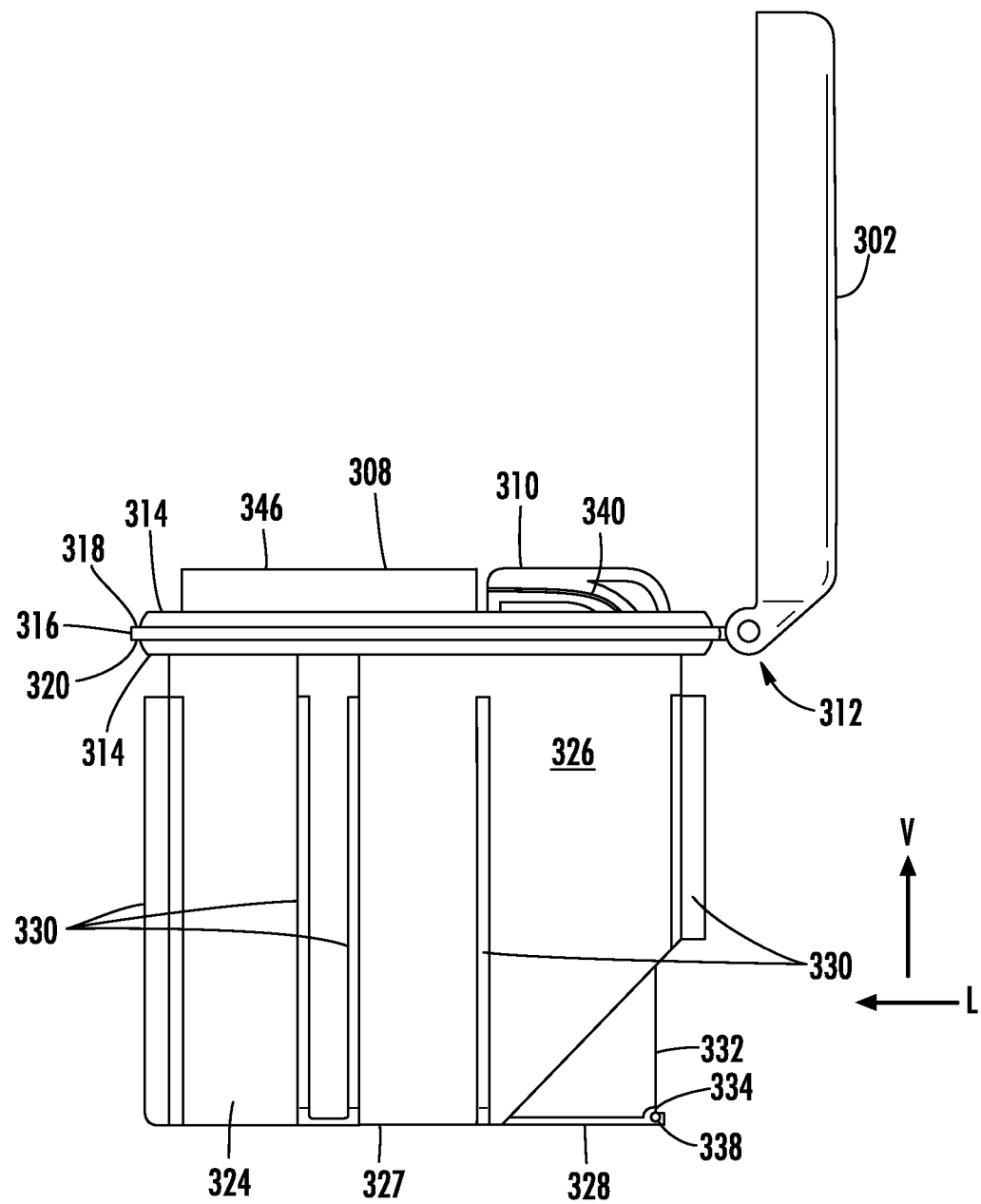
FIG. 23 is a side view of the dispenser shown in FIG. 22 with the base removed.
Figure 24:
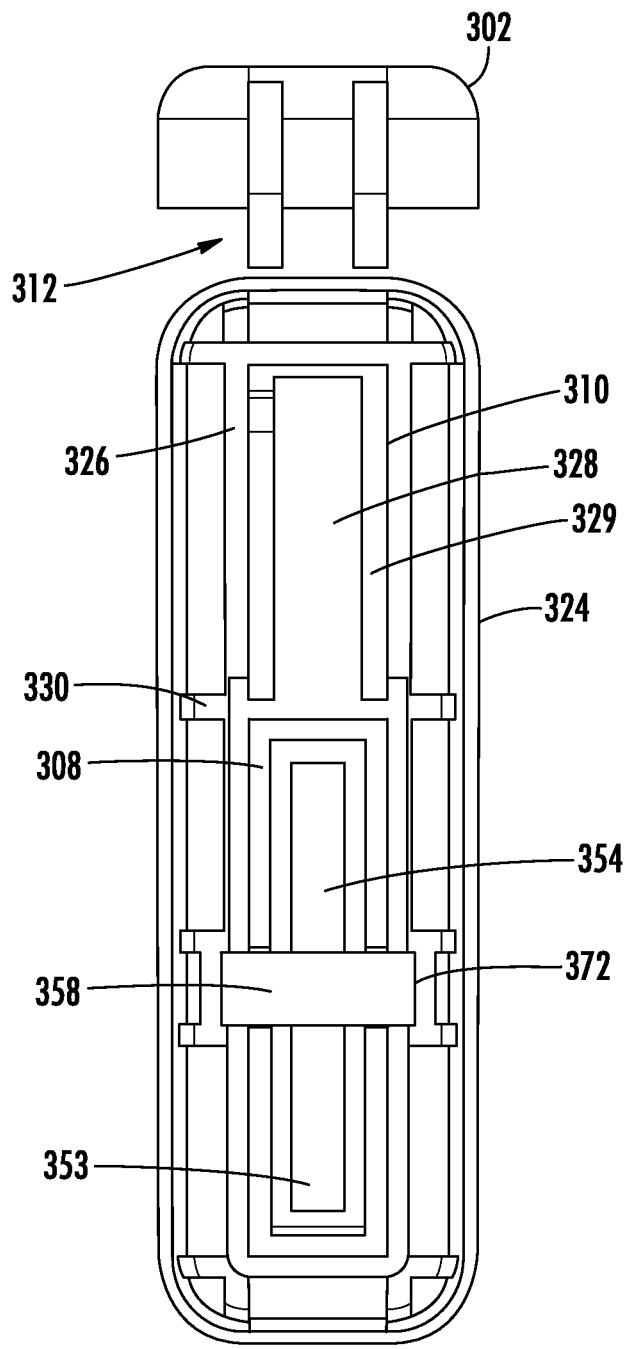
FIG. 24 is a bottom view of the dispenser shown in FIG. 23.
Figure 25:
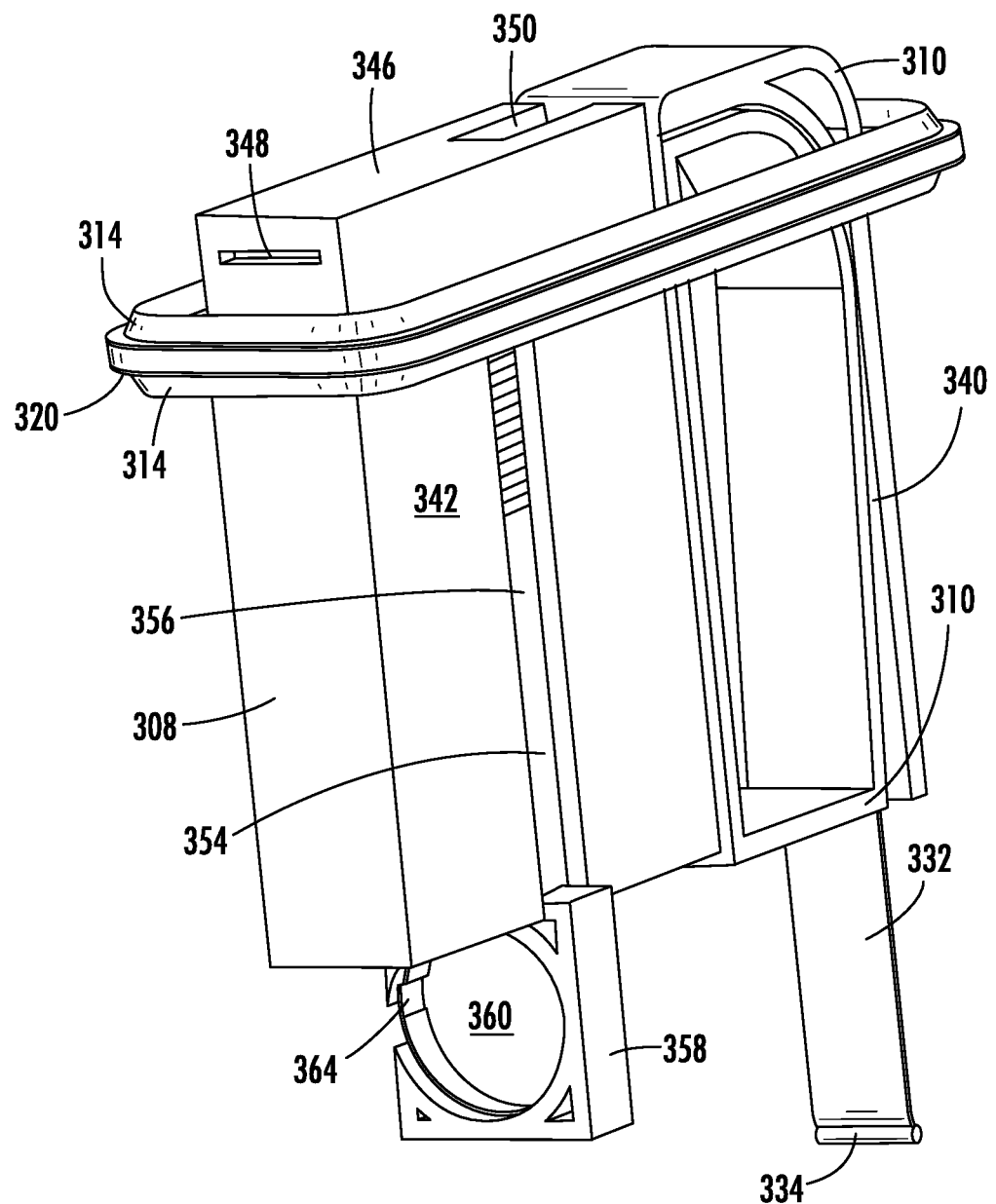
FIG. 25 is a first side perspective view of a dispenser housing, guide housing, pusher blade, pusher bar, and guide according to an embodiment of the present invention.
Figure 26:
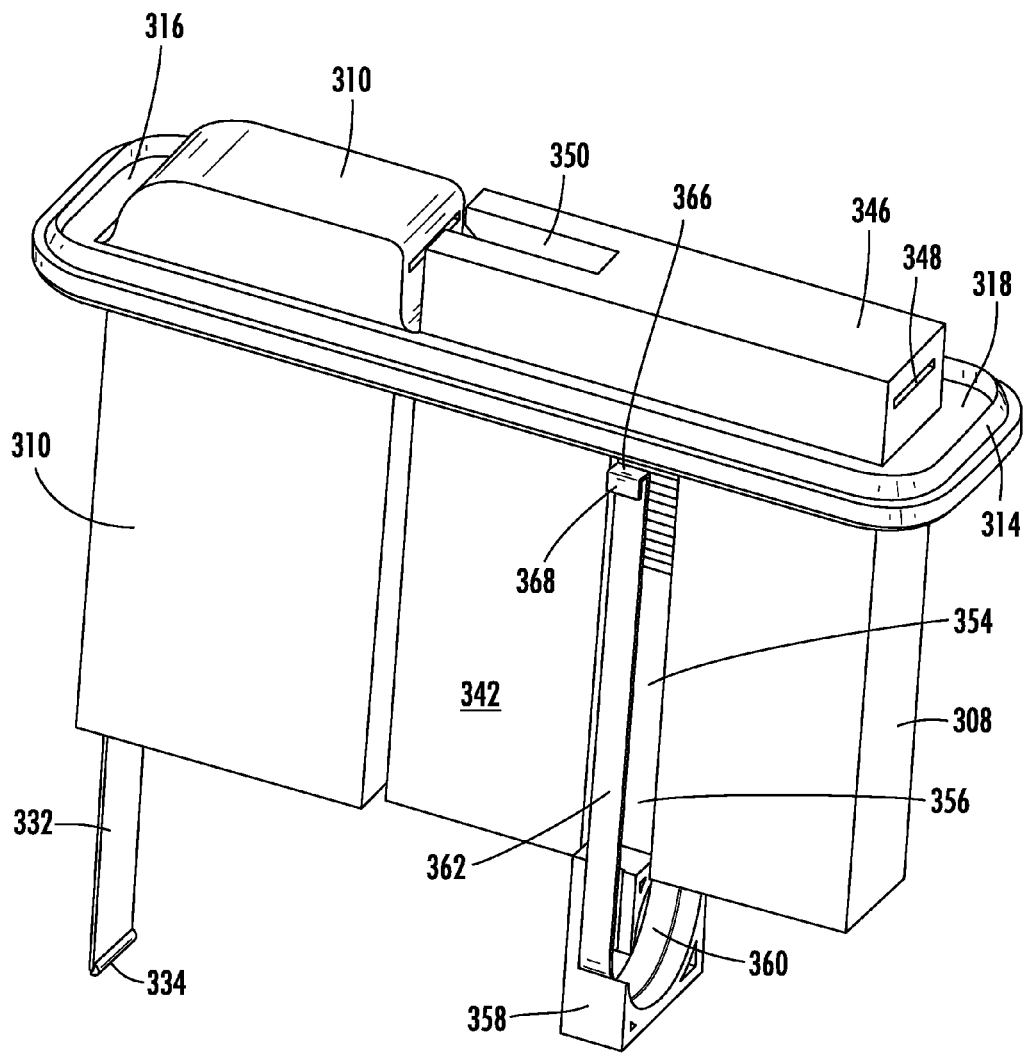
FIG. 26 is a second side perspective view of a dispenser housing, guide housing, pusher blade, pusher bar, guide, and spring according to an embodiment of the present invention.
Figure 27:
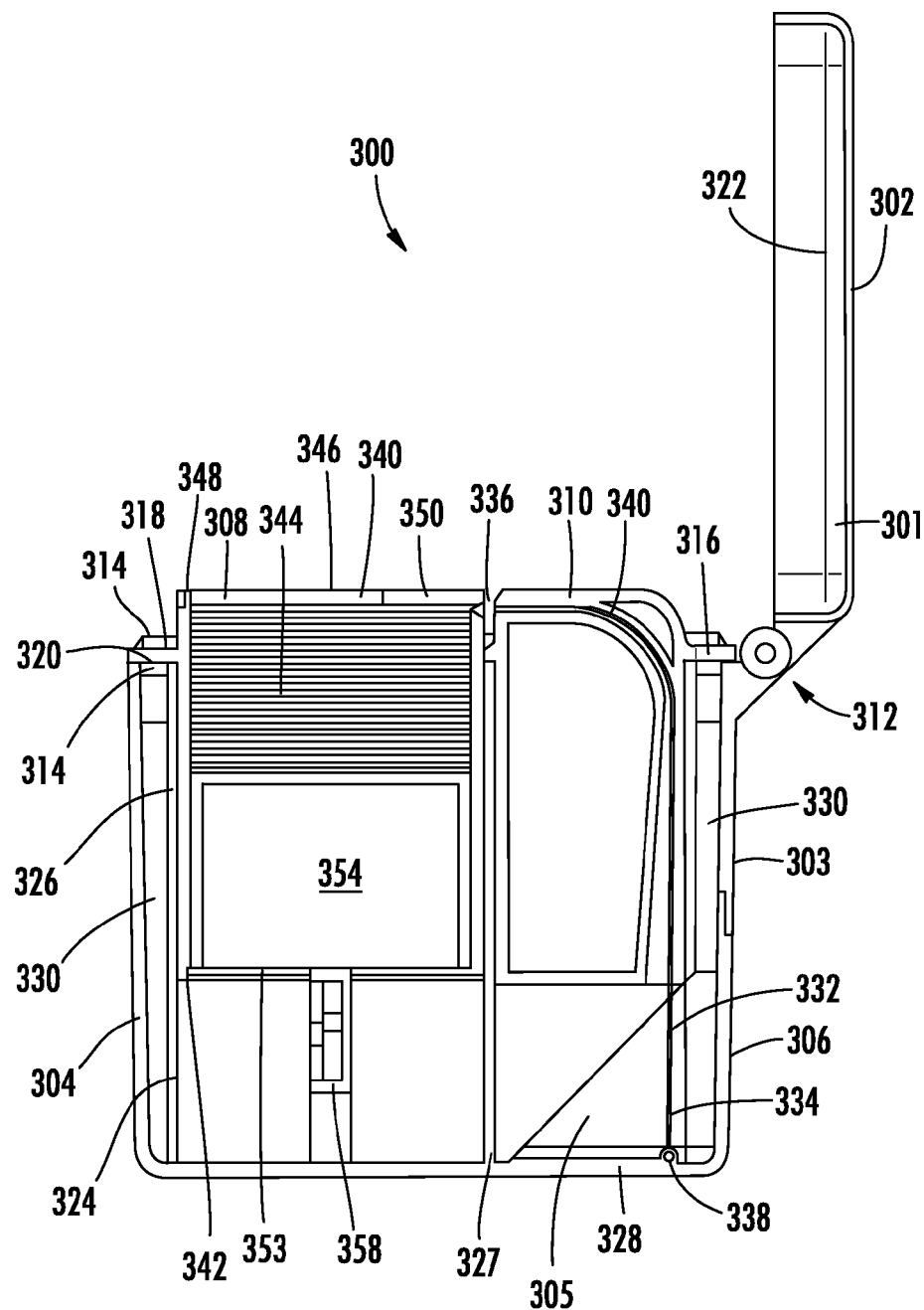
FIG. 27 is a cross sectional view of the dispenser shown in FIG. 22.

Another embodiment of a dispenser assembly 300 is shown in FIGS. 22-27. As shown in FIG. 22, the dispenser assembly 300 includes a container 301 having a lid 302 and an base 304, a flexible member 306, a dispenser housing 308, and a guide housing 310. The base includes a sidewall 303 that defines an interior region 305. The lid 302 is attached to the base 304 by a hinge 312 that allows the lid 302 to move from an open position, as shown in FIG. 22, to a closed position. When in a closed position, at least a portion of the lid 302 may engage a seal 314 to control the ingress of moisture into the dispenser assembly 300. As shown in FIG. 22, according to an embodiment, the seal 314 may be gasket that is positioned about an upper peripheral surface 316 of the dispenser housing 308. For example, as shown in FIGS. 22 and 25, the seal 314 is secured about top and lower surfaces 318, 320 of the upper peripheral surface 316 of the dispenser housing 308. However, the seal 314 may be placed at a variety of locations, such as along a peripheral edge of the dispenser housing 308 or base 304, or used in combination with other seals, such as seals that may abut the top wall 322 of the lid 302. According to certain embodiments, the seal 314 may be formed of an elastomeric material.

As shown in FIGS. 23 and 24, according to certain embodiments, an inner receptacle 324 is positioned within the interior region 305 of the base 304. Although shown as a separated component, according to certain embodiments, the base 304 and inner receptacle 324 may be one integral part. The inner receptacle 324 includes a sidewall 326 and a lever 328. According to an embodiment, the lever 328 may extend from a base portion 327 of the inner receptacle 324. Additionally, the sidewall 326 may be configured to allow a user to press on the flexible member 306 so as to displace, bend, or rotate the lever 328.

The sidewall 326 may generally define an interior area 329 for the placement of at least a portion of the dispenser housing 308 and the guide housing 310. The dispenser housing 308 and guide housing 310 may be secured to the inner receptacle 324 and/or base 304, such as, for example, by an interference fit, a snap fit, a mechanical fastener, such as by a screw or pin, an adhesive, and/or a weld, among others. Additionally, as shown by at least FIG. 26, a portion of the guide housing 310 may protrude through an opening in the upper peripheral surface 316 of the dispenser housing 308.

According to certain embodiments, the sidewall 326 of the inner receptacle 324 may include a plurality of tapered ribs 330 that are configured to create a press or interference fit for securing the base 304 to the inner receptacle 324. Additionally, the flexible member 306 may be configured so that a portion of the flexible member 306 is positioned and/or pressed between one or more ribs 330 and the base 304 so as to secure the flexible member 306 to the dispenser assembly 300.

The lever 328 of the inner receptacle 324 is operably connected to a first end 334 of a pusher blade 332, such as for example, by an aperture 338 into which the first end 334 of the pusher blade 332 is secured, such as by a press or snap fit. The pusher blade 332 extends from the lever 328 and into, and along, a slot 340 of the guide housing 310. The lever 328 is configured to be bent, deformed, distorted or rotated from a first, rest position to a second position so that the pusher blade 332 in the general vicinity of the first end 334 is generally displaced in the "V" direction (as shown in FIG. 23), and thereby displace a second end 336 of the pusher blade 332 so as to dispense product, such as strips 12, from the dispenser housing 308, as discussed below.

The dispenser housing 308 may include an upper portion 346, a body portion 342, and an upper peripheral surface 316. The body portion 342 may include sidewalls 326 that generally define an interior region 344 that is configured to receive the placement of a stack of strips 11. The upper portion 346 of the body portion 342 includes a dispensing opening 348 through which individual strips 12 may be dispensed to a user. According to certain embodiments, the upper portion 346 may include a slot 350 that is configured to receive the moveable insertion of a second end 336 of the pusher blade 332. A lower portion 352 of the body portion 342, such as a feeding end, may include a lower opening 353 through which stacks of strips 11 may be inserted into the interior region 344. A pusher bar 354 may also be inserted into at least a portion of the interior region 344 through the lower opening 353 and into the interior area after the insertion of the stack of strips 11 into the interior region 344.

According to certain embodiments, the body portion 342 of the dispenser housing 308 includes one or more slots 356 that allow and/or guide the movement of a guide 358 along the dispensing housing 308. Further, according to certain embodiments, the guide 358, which abuts the pusher bar 354, may be secured to a spring 362, such as, for example being secured at or around a first end 364 of the spring 362. The spring 362 biases the guide 358, and thus the pusher bar 354 and stack of strips 11, toward the dispensing end of the dispenser housing 308. More specifically, according to certain embodiments, the guide 358 may include an aperture 360 in which the first end 364 of the spring 362 may be secured to and/or positioned in the guide 358, and which allows for portions of the spring 362 to recoil into the aperture 360 as the guide 358 is displaced toward the upper portion 346. The second end 366 of the spring 362 may include a hook 368 that is attached to an opening or catch of the inner receptacle 324, base 304, or other portion of the dispenser housing 308. Additionally, according to certain embodiments, the guide 358 may be an integral part of the pusher bar 354, or may be replaced by the spring 362 to the pusher bar 354. Additionally, the inner receptacle 324 may include a slot 372 that assists in guiding the movement of the guide 358 generally in the "V" direction.

In use, individual strips 12 may be dispensed from the dispenser assembly 300 by a user pressing on the flexible member 306 so as to generally displace the portion of the pusher blade 332 in the vicinity of the first end 334 in the "V" direction, such as by a user pressing on the flexible member 306 so as to upwardly displace, bend, or rotate the lever 328. This movement of the pusher blade 332 results in at least a portion of the pusher blade 332 being moved along the slot 340 so that the second end 336 of the pusher blade 332 is generally displaced in the "L" direction (as indicated by FIG. 23). As the second end 336 of the pusher blade 332 is generally displaced in the "L" direction, the second end 336 of the pusher blade 332 comes into contact with an end portion of the strip 12 that is atop the stack of strips 11, thereby moving the top strip 12 in the "L" direction so that at least a portion of the strip 12 will extend out of the dispensing opening 348 of the dispenser housing 308. With at least a portion of the strip 12 extending through the dispensing opening 348, the user may be able to grip the strip 12 and remove the strip 12 from the dispenser assembly 300. Alternatively, according to certain embodiments, the pusher blade 332 may extend at least far enough into the dispenser housing 308 so that the entire strip 12 is pushed out of the dispenser housing 308.

After a strip 12 has been dispensed from the dispenser assembly 300, the spring 362 forces the guide 358 to move the pusher bar 354, and thus the stack of strips 11, toward the upper portion 346 of the body portion 342 so as to fill the space that was previously occupied by the now dispensed strip 12. Therefore, after a strip 12 has been dispensed from the dispenser assembly 300, the spring 362 assists in moving the stack of strips 11 so that the strip 12 that is now at the top of the stack of strip 11 is positioned adjacent to the dispensing opening 348 and in position for engagement with the pusher blade 332.

When the user releases pressure on the flexible member 306, and thus the lever 328, the lever 328 will generally return to its pre-displaced position, thereby retracting at least a portion of the pusher bar 354 in the general vicinity of the second end 336 back into the guide housing 310. However, according to certain embodiments, at least a portion of the pusher blade 332 in proximity to the second end 336 may or may not continue to extend out of the guide housing 310 after the user has releases pressure on the flexible member 306 so that the lever 328 generally returns to its first position.

The dispenser assembly 300 may be refilled with a stack of strips 11. For example, according to certain embodiments, after the supply of strips 12 have been depleted or are no longer going to be used, individual or groups of components of the dispenser assembly 300 may be removed to be refilled with strips 12 or a stack of strips 11 and/or be replaced with new components. For example, according to certain embodiments, the base 304 and lid 302 may be placed on a new inner receptacle 324 that includes a new, previously used, or a combination thereof, dispenser housing 308, guide housing 310, seal 314, pusher bar 354, spring 362, guide 358, and a stack of strips 11 or an individual strip 12. According to such an embodiment, the flexible member 306 may be reused or be replaced with a new flexible member 306. Similarly, according to certain embodiments, the dispenser housing 308 may be removed from the inner receptacle 324, such as for example by overcoming a snap or interference fit or the removal of a mechanical fastener, so as to be replaced with a new dispenser housing 308 containing a stack of strips 11, or may be refilled with additional strips 12. Accordingly, other individual components may also be removed and/or replaced, such as, for example, providing a new seal 314 with a new dispenser housing 308.

In any of the embodiments described above, portions of the dispenser assemblies 10, 200, 300 could be formed of a desiccant plastic material, such as that disclosed in U.S. Pat. Nos. 5,911,937; 6,214,255; 6,130,263; 6,080,350; 6,174,952; 6,124,006; and 6,221,446, each of which is incorporated by reference herein as if fully set forth. For example, in one embodiment the pusher bar 64, 262, 354 could be formed of a desiccant plastic material.

While embodiments of the invention have been described in detail above, the invention is not limited to the specific embodiments described, which should be considered as merely exemplary.

| Reference Number List | |
|---|---|
| 10 | Dispenser Assembly |
| 11 | Stack of Strips |
| 12 | Individual Strip |
| 13 | Contact Corner |
| 14 | First End (of 11) |
| 16 | Second End (of 11) |
| 18 | Dispensed End (of 12) |
| 20 | Container |
| 22 | Base |
| 24 | Lid |
| 26 | Hinge |
| 28 | Bottom Wall (of 22) |
| 30 | Side Wall (of 22) |
| 32 | Top Wall (of 24) |
| 34 | Side Wall (of 24) |
| 38 | Upper Edge (of 30) |
| 50 | Cartridge |
| 52 | Interior (of 50) |
| 54 | Dispensing Opening |
| 55 | Feeding End (of 50) |
| 56 | Dispensing End (of 50) |
| 58 | Slider Arm Slot |
| 60 | Clearance Slot |
| 62 | Guide Slot |
| 64 | Pusher Bar |
| 66 | Access Opening |
| 70 | Packaging |
| 80 | Cartridge Housing |
| 82 | Recess |
| 84 | Guide Slot |
| 86 | Feeding End (of 80) |
| 88 | Dispensing End (of 80) |
| 90 | Guide |
| 92 | Rail |
| 94 | Body (of 90) |
| 96 | Spring |
| 98 | First End (of 96) |
| 100 | Second End (of 96) |
| 102 | Protrusion |
| 104 | Catch |
| 106 | Channel |
| 108 | Access Slot |
| 112 | Top Wall (of 106) |
| 114 | Slider Arm Slot |
| 116 | Side Wall of (106) |
| 120 | Slider |
| 122 | Body (of 120) |
| 124 | Actuation Portion |
| 126 | Arm |
| 130 | Interface Electronics |
| 132 | Processor |
| 134 | Display |
| 136 | Port |
| 138 | Memory |
| 140 | Buttons |
| 142 | Outside Device |
| 144 | Display (of 142) |
| 146 | Track |
| 148 | Track |
| 200 | Dispenser Assembly |
| 201 | Container |
| 202 | Lid |
| 203 | Bottom Wall |
| 204 | Base |
| 205 | Interior Area (of 204) |
| 206 | Grip |
| 208 | Cartridge |
| 209 | Cartridge Hook |
| 210 | Sidewall (of 204) |
| 214 | Attachment Member |
| 216 | First End (of 214) |
| 218 | Second End (of 214) |
| 220 | Guide |
| 222 | Guide Slot |
| 224 | Rail |
| 226 | Guide Body |
| 228 | First Wall |
| 230 | Second Wall |
| 232 | Latch (of 220) |
| 234 | Hook |
| 236 | Protrusion (of 220) |
| 238 | Spring |
| 240 | First End (of 238) |
| 242 | Second End (of 238) |
| 244 | Catch |
| 246 | Channel (of 214) |
| 247 | Slider Body |
| 248 | Slider |
| 249 | Actuator Portion |
| 250 | Top Wall |
| 251 | Protrusion (of 248) |
| 252 | Slider Arm Slot |
| 253 | Bracket |
| 254 | Slider Arm (of 248) |
| 256 | Interior Region |
| 258 | Bottom Portion (of 208) |
| 260 | Sidewalls (of 208) |
| 262 | Pusher Bar |
| 264 | Grip Protrusion |
| 265 | Grip Interface |
| 266 | Protrusion (of 214) |
| 268 | Cover |
| 270 | Inner Sidewall (of 268) |
| 272 | Orifice |
| 274 | Slot |
| 276 | Dispensing Opening |
| 277 | Recessed Area (of 214) |
| 278 | Seal |
| 280 | Upper Wall (of 208) |
| 282 | Upper Lip |
| 283 | Recess (of 214) |
| 284 | Spring |
| 286 | Connector |
| 287 | Recessed Surface |
| 290 | Dispenser Assembly |
| 291 | Pocket (of 294) |
| 292 | Base |
| 293 | Recessed Surface (of 296) |
| 294 | Lid |
| 295 | Interface electronics |
| 296 | Electronics Housing |
| 297 | Interior Wall |
| 298 | Display |
| 299 | Port |
| 300 | Dispenser Assembly |
| 301 | Container |
| 302 | Lid |
| 303 | Sidewall (of 304) |
| 304 | Base |
| 305 | Interior Region (of 304) |
| 306 | Flexible Member |
| 308 | Dispenser Housing |
| 310 | Guide Housing |
| 312 | Hinge |
| 314 | Seal |
| 316 | Upper Peripheral Surface |
| 318 | Top Surface |
| 320 | Lower Surface |
| 322 | Top Wall |
| 324 | Inner Receptacle |
| 326 | Sidewall |
| 327 | Base Portion |
| 328 | Lever |
| 329 | Interior Area (of 324) |
| 330 | Rib |
| 332 | Pusher Blade |
| 334 | First End (of 332) |
| 336 | Second End (of 332) |
| 338 | Aperture (of 328) |
| 340 | Slot |

-continued

| Reference Number List | |
|---|---|
| 342 | Body Portion |
| 344 | Interior Region |
| 346 | Upper Portion (of 308) |
| 348 | Dispensing Opening (of 308) |
| 350 | Slot (of 346) |
| 352 | Lower Portion (of 342) |
| 353 | Lower Opening |
| 354 | Pusher Bar |
| 356 | Slot (of 342) |
| 358 | Guide |
| 360 | Aperture (of 358) |
| 362 | Spring |
| 364 | First End (of 362) |
| 366 | Second End (of 362) |
| 368 | Hook |
| 372 | Slot (of 324) |

What is claimed is:

1. A dispenser assembly comprising:
a container having a base and lid, the base having a bottom wall and a side wall that generally define an interior space;
optionally, a hinge joining the base and the lid;
a cartridge housing positioned within the interior space, the cartridge housing having a recess;
a dispensing cartridge having a dispensing end, a feeding end, and an interior, at least a portion of the dispensing cartridge positioned within the recess of the cartridge housing, the interior of the dispensing cartridge configured to receive the placement of a stack of strips, the dispenser cartridge having a dispensing opening configured to dispense a strip from the stack of strips;
a pusher bar at least partially positioned in the interior of the dispensing cartridge;
a guide comprising a guide rail, wherein the guide is biased by a first spring to press the pusher bar toward the dispensing end of the dispensing cartridge; and
a slider having a slider arm, at least a portion of the slider being housed in a channel formed in the cartridge housing, the channel configured for the slideable movement of the slider from a first, non-dispensing, position to a second, dispensing, position.

2. The dispenser assembly of claim 1, wherein the dispenser assembly includes a seal to control the ingress of moisture into at least a portion of the dispenser assembly.

3. The dispenser assembly of claim 2, wherein at least a portion of the seal is positioned about a peripheral edge of the base, lid, or dispensing cartridge.

4. The dispenser assembly of claim 3, wherein the seal is made of an elastomeric material.

5. The dispenser assembly of claim 1, wherein a seal is formed between the lid and the base.

6. The dispenser assembly of claim 1, wherein the dispensing cartridge includes a clearance slot at the dispensing end of the dispensing cartridge, the clearance slot positioned and configured to allow the pivotable movement of at least a portion of a strip from the stack of strips as the strip is being dispensed.

7. The dispenser assembly of claim 1, wherein the dispensing cartridge includes a slider arm slot configured to receive the slider arm.

8. The dispenser assembly of claim 1, wherein the dispensing cartridge includes a guide slot, the guide slot configured to receive the insertion of the guide.

9. The dispenser assembly of claim 8, wherein at least a portion of the guide rail being configured to be inserted into the guide slot and for engagement with the pusher bar.

10. The dispenser assembly of claim 8, wherein the cartridge housing includes a guide slot that aligns with the guide slot of the dispensing cartridge.

11. The dispenser assembly of claim 1, wherein the slider includes a body portion and an actuator portion.

12. The dispenser assembly of claim 11, further including a second spring, the second spring configured to bias the slider in a first position.

13. The dispenser assembly of claim 1, wherein the dispensing cartridge is removable from the dispenser assembly so that the dispensing cartridge can be replaced with another dispensing cartridge or refilled with a stack of strips.

14. The dispenser assembly of claim 1, wherein the dispenser assembly includes interface electronics, the interface electronics including a processor for processing information contained in a sample from a user on a dispensed strip from the dispenser assembly.

15. The dispenser assembly of claim 14, wherein the interface electronics includes a display.

16. The dispenser assembly of claim 14, wherein at least a portion of the interface electronics are incorporated into the lid.

17. The dispenser assembly of claim 14, wherein the dispensing assembly includes a port that is operably connected to the processor, the port configured to receive the insertion of the dispensed strip containing the sample, the port configured to detect information contained in the sample on the dispensed strip.

18. The dispensing assembly of claim 17, wherein the detected information relates to blood glucose.

19. The dispenser assembly of claim 17, wherein the processor processes information detected in the sample, at least a portion of the processed information being displayed on the display.

20. The dispenser assembly of claim 14, wherein the information detected from the sample is communicated to an outside device, the outside device including a processer to process the communicated information.

21. The dispenser assembly of claim 20, wherein the outside device includes a display to display information related to the information communicated from the interface electronics.

* * * * *